United States Patent [19]
Jefferson et al.

[11] Patent Number: 5,879,906
[45] Date of Patent: Mar. 9, 1999

[54] GLUCURONIDE REPRESSORS AND USES THEREOF

[75] Inventors: Richard A. Jefferson, Queanbeyan; Katherine J. Wilson, Townsville; Michael Leader, Page, all of Australia

[73] Assignee: Cambia Biosystems LLC, Bellevue, Wash.

[21] Appl. No.: 882,704

[22] Filed: Jun. 25, 1997

Related U.S. Application Data

[60] Provisional application No. 60/020,621 Jun. 26, 1996.

[51] Int. Cl.⁶ .......................... C12P 21/00; C12N 15/70; C12N 5/00; C07H 21/04
[52] U.S. Cl. .................. 435/69.1; 435/91.41; 435/243; 435/320.1; 435/325; 435/410; 536/23.4; 536/23.5; 536/24.1
[58] Field of Search ....................... 435/69.1, 91.41, 435/243, 320.1, 325, 410; 536/23.4, 23.5, 24.1

[56] References Cited

U.S. PATENT DOCUMENTS 5,268,463  12/1993  Jefferson ................. 536/23.7

OTHER PUBLICATIONS

Blanco et al., "Cloning and Endonuclease Restriction Analysis of uidA and uidR Genes in *Escherichia coli* K–12: Determination of Transcription Direction for the uidA Gene," *Journal of Bacteriology* 149(2):587–594, 1982.

Blanco, "Transcriptional and translational signals of the uidA gene in *Escherichia coli* K12," *Mol Gen Genet* 208:490–498, 1987.

Ritzenthaler et al., "Interchangeability of Repressors for the Control of the uxu and uid Operons in *E. coli* K12," *Mol Gen Genet* 191:263–270, 1983.

Wilson and Jefferson, "The GusR repressor of *Escherichia Coli*," *EMBL Database Entry Ecuidaa; Accession No. M 14641*(Version 8), 1995.

*Primary Examiner*—James Ketter
*Assistant Examiner*—William Sandals
*Attorney, Agent, or Firm*—Seed and Berry LLP

[57] ABSTRACT

Clones containing a sequence encoding a glucuronide repressor are described. The nucleotide and amino acid sequences of a repressor (gusR) are presented. A glucuronide repressor is used to control expression of a transgene, detect glucuronides in a sample, and isolate glucuronides from a sample, among other uses.

38 Claims, 27 Drawing Sheets

Purification of GUSR:
Phenylthio-β-D-glucuronide-Sepharose CL6B

Purification of GUSR:
Ni$^{2+}$-IDA-Sepharose (IMAC)

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 585 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATGGATAACA  TGCAGACTGA  AGCACAACCG  ACACGGACCC  GGATCCTCAA  TGCTGCCAGA     60

GAGATTTTTT  CAGAAAATGG  ATTTCACAGT  GCCTCGATGA  AAGCCATCTG  TAAATCTTGC    120

GCCATTAGTC  CCGGGACGCT  CTATCACCAT  TTCATCTCCA  AAGAAGCCTT  GATTCAGGCG    180

ATTATCTTAC  AGGACCAGGA  GAGGGCGCTG  GCCCGTTTCC  GGGAACCGAT  TGAAGGGATT    240

CATTTCGTTG  ACTATATGGT  CGAGTCCATT  GTCTCTCTCA  CCCATGAAGC  CTTTGGACAA    300

CGGGCGCTGG  TGGTTGAAAT  TATGGCGGAA  GGGATGCGTA  ACCCACAGGT  CGCCGCCATG    360

CTTAAAAATA  AGCATATGAC  GATCACGGAA  TTTGTTGCCC  AGCGGATGCG  TGATGCCCAG    420

CAAAAAGGCG  AGATAAGCCC  AGACATCAAC  ACGGCAATGA  CTTCACGTTT  ACTGCTGGAT    480

CTGACCTACG  GTGTACTGGC  CGATATCGAA  GCGGAAGACC  TGGCGCGTGA  AGCGTCGTTT    540

GCTCAGGGAT  TACGCGCGAT  GATTGGCGGT  ATCTTAACCG  CATCC                    585
```

( 2 ) INFORMATION FOR SEQ ID NO:2:

( i ) SEQUENCE CHARACTERISTICS:
        ( A ) LENGTH: 195 amino acids
        ( B ) TYPE: amino acid
        ( C ) STRANDEDNESS:

(D) TOPOLOGY: linear (xi) SEQUENCE DESCRIPTION: SEQ ID NO:2:

```
Met Asp Asn Met Gln Thr Glu Ala Gln Pro Thr Arg Thr Arg Ile Leu
 1               5                  10                   15
Asn Ala Ala Arg Glu Ile Phe Ser Glu Asn Gly Phe His Ser Ala Ser
            20                  25                  30
Met Lys Ala Ile Cys Lys Ser Cys Ala Ile Ser Pro Gly Thr Leu Tyr
        35                  40                  45
His His Phe Ile Ser Lys Glu Ala Leu Ile Gln Ala Ile Ile Leu Gln
    50                  55                  60
Asp Gln Glu Arg Ala Leu Ala Arg Phe Arg Glu Pro Ile Glu Gly Ile
65                  70                  75                  80
His Phe Val Asp Tyr Met Val Glu Ser Ile Val Ser Leu Thr His Glu
                85                  90                  95
Ala Phe Gly Gln Arg Ala Leu Val Val Glu Ile Met Ala Glu Gly Met
            100                 105                 110
Arg Asn Pro Gln Val Ala Ala Met Leu Lys Asn Lys His Met Thr Ile
        115                 120                 125
Thr Glu Phe Val Ala Gln Arg Met Arg Asp Ala Gln Gln Lys Gly Glu
    130                 135                 140
Ile Ser Pro Asp Ile Asn Thr Ala Met Thr Ser Arg Leu Leu Leu Asp
145                 150                 155                 160
Leu Thr Tyr Gly Val Leu Ala Asp Ile Glu Ala Glu Asp Leu Ala Arg
                165                 170                 175
Glu Ala Ser Phe Ala Gln Gly Leu Arg Ala Met Ile Gly Gly Ile Leu
            180                 185                 190
Thr Ala Ser
    195
```

(2) INFORMATION FOR SEQ ID NO:3:

(i) SEQUENCE CHARACTERISTICS:
(A) LENGTH: 390 base pairs
(B) TYPE: nucleic acid
(C) STRANDEDNESS: single
(D) TOPOLOGY: linear (xi) SEQUENCE DESCRIPTION: SEQ ID NO:3:

```
TTCTCTCTCT TTTTCGGCGG GCTGGTGATA ACTGTGCCCG CGTTTCATAT CGTAATTTCT        60
CTGTGCAAAA ATTATCCTTC CCGGCTTCGG AGAATTCCCC CCAAAATATT CACTGTAGCC       120
ATATGTCATG AGAGTTTATC GTTCCCAATA CGCTCGAACG AACGTTCGGT TGCTTATTTT       180
ATGGCTTCTG TCAACGCTGT TTTAAAGATT AATGCGATCT ATATCACGCT GTGGGTATTG       240
CAGTTTTTGG TTTTTTGATC GCGGTGTCAG TTCTTTTTAT TTCCATTTCT CTTCCATGGG       300
TTTCTCACAG ATAACTGTGT GCAACACAGA ATTGGTTAAC TAATCAGATT AAAGGTTGAC       360
CAGTATTATT ATCTTAATGA GGAGTCCCTT                                        390
```

(2) INFORMATION FOR SEQ ID NO:4:

(i) SEQUENCE CHARACTERISTICS:
(A) LENGTH: 7742 base pairs
(B) TYPE: nucleic acid
(C) STRANDEDNESS: single
(D) TOPOLOGY: linear (xi) SEQUENCE DESCRIPTION: SEQ ID NO:4:

```
CTGGTCAGAA ATATGGCGTT TGACCTGGGT GAAAAAATA TTCGGGTAAA TGGCATTGCG          60
```

-continued

| | | | | | | |
|---|---|---|---|---|---|---|
| CCGGGGGCAA | TATTAACCGA | TGCCCTGAAA | TCCGTTATTA | CACCAGAAAT | TGAACAAAAA | 120 |
| ATGTTACAGC | ACACGCCGAT | CAGACGTCTG | GGCCAACCGC | AAGATATTGC | TAACGCAGCG | 180 |
| CTGTTCCTTT | GCTCGCCTGC | TGCGAGCTGG | GTAAGCGGAC | AAATTCTCAC | CGTCTCCGGT | 240 |
| GGTGGGGTAC | AGGAGCTCAA | TTAATACACT | AACGGACCGG | TAAACAACCG | TGCGTGTTGT | 300 |
| TTACCGGGAT | AAACTCATCA | ACGTCTCTGC | TAAATAACTG | GCAGCCAAAT | CACGGCTATT | 360 |
| GGTTAACCAA | TTTCAGAGTG | AAAAGTATAC | GAATAGAGTG | TGCCTTCGCA | CTATTCAACA | 420 |
| GCAATGATAG | GCGCTCACCT | GACAACGCGG | TAAACTAGTT | ATTCACGCTA | ACTATAATGG | 480 |
| TTTAATGATG | GATAACATGC | AGACTGAAGC | ACAACCGACA | CGGACCCGGA | TCCTCAATGC | 540 |
| TGCCAGAGAG | ATTTTTTCAG | AAAATGGATT | TCACAGTGCC | TCGATGAAAG | CCATCTGTAA | 600 |
| ATCTTGCGCC | ATTAGTCCCG | GGACGCTCTA | TCACCATTTC | ATCTCCAAAG | AAGCCTTGAT | 660 |
| TCAGGCGATT | ATCTTACAGG | ACCAGGAGAG | GGCGCTGGCC | CGTTTCCGGG | AACCGATTGA | 720 |
| AGGGATTCAT | TTCGTTGACT | ATATGGTCGA | GTCCATTGTC | TCTCTCACCC | ATGAAGCCTT | 780 |
| TGGACAACGG | GCGCTGGTGG | TTGAAATTAT | GGCGGAAGGG | ATGCGTAACC | CACAGGTCGC | 840 |
| CGCCATGCTT | AAAAATAAGC | ATATGACGAT | CACGGAATTT | GTTGCCCAGC | GGATGCGTGA | 900 |
| TGCCCAGCAA | AAAGGCGAGA | TAAGCCCAGA | CATCAACACG | GCAATGACTT | CACGTTTACT | 960 |
| GCTGGATCTG | ACCTACGGTG | TACTGGCCGA | TATCGAAGCG | GAAGACCTGG | CGCGTGAAGC | 1020 |
| GTCGTTTGCT | CAGGGATTAC | GCGCGATGAT | TGGCGGTATC | TTAACCGCAT | CCTGATTCTC | 1080 |
| TCTCTTTTTC | GGCGGGCTGG | TGATAACTGT | GCCCGCGTTT | CATATCGTAA | TTTCTCTGTG | 1140 |
| CAAAAATTAT | CCTTCCCGGC | TTCGGAGAAT | TCCCCCCAAA | ATATTCACTG | TAGCCATATG | 1200 |
| TCATGAGAGT | TTATCGTTCC | CAATACGCTC | GAACGAACGT | TCGGTTGCTT | ATTTTATGGC | 1260 |
| TTCTGTCAAC | GCTGTTTTAA | AGATTAATGC | GATCTATATC | ACGCTGTGGG | TATTGCAGTT | 1320 |
| TTTGGTTTTT | TGATCGCGGT | GTCAGTTCTT | TTTATTTCCA | TTTCTCTTCC | ATGGGTTTCT | 1380 |
| CACAGATAAC | TGTGTGCAAC | ACAGAATTGG | TTAACTAATC | AGATTAAAGG | TTGACCAGTA | 1440 |
| TTATTATCTT | AATGAGGAGT | CCCTTATGTT | ACGTCCTGTA | GAAACCCCAA | CCCGTGAAAT | 1500 |
| CAAAAAACTC | GACGGCCTGT | GGGCATTCAG | TCTGGATCGC | GAAAACTGTG | GAATTGATCA | 1560 |
| GCGTTGGTGG | GAAAGCGCGT | TACAAGAAAG | CCGGGCAATT | GCTGTGCCAG | GCAGTTTTAA | 1620 |
| CGATCAGTTC | GCCGATGCAG | ATATTCGTAA | TTATGCGGGC | AACGTCTGGT | ATCAGCGCGA | 1680 |
| AGTCTTTATA | CCGAAAGGTT | GGGCAGGCCA | GCGTATCGTG | CTGCGTTTCG | ATGCGGTCAC | 1740 |
| TCATTACGGC | AAAGTGTGGG | TCAATAATCA | GGAAGTGATG | GAGCATCAGG | GCGGCTATAC | 1800 |
| GCCATTTGAA | GCCGATGTCA | CGCCGTATGT | TATTGCCGGG | AAAAGTGTAC | GTATCACCGT | 1860 |
| TTGTGTGAAC | AACGAACTGA | ACTGGCAGAC | TATCCCGCCG | GGAATGGTGA | TTACCGACGA | 1920 |
| AAACGGCAAG | AAAAAGCAGT | CTTACTTCCA | TGATTTCTTT | AACTATGCCG | GGATCCATCG | 1980 |
| CAGCGTAATG | CTCTACACCA | CGCCGAACAC | CTGGGTGGAC | GATATCACCG | TGGTGACGCA | 2040 |
| TGTCGCGCAA | GACTGTAACC | ACGCGTCTGT | TGACTGGCAG | GTGGTGGCCA | ATGGTGATGT | 2100 |
| CAGCGTTGAA | CTGCGTGATG | CGGATCAACA | GGTGGTTGCA | ACTGGACAAG | GCACTAGCGG | 2160 |
| GACTTTGCAA | GTGGTGAATC | CGCACCTCTG | GCAACGGGT | GAAGGTTATC | TCTATGAACT | 2220 |
| GTGCGTCACA | GCCAAAAGCC | AGACAGAGTG | TGATATCTAC | CCGCTTCGCG | TCGGCATCCG | 2280 |
| GTCAGTGGCA | GTGAAGGGCG | AACAGTTCCT | GATTAACCAC | AAACCGTTCT | ACTTTACTGG | 2340 |
| CTTTGGTCGT | CATGAAGATG | CGGACTTACG | TGGCAAAGGA | TTCGATAACG | TGCTGATGGT | 2400 |
| GCACGACCAC | GCATTAATGG | ACTGGATTGG | GGCCAACTCC | TACCGTACCT | CGCATTACCC | 2460 |

```
TTACGCTGAA  GAGATGCTCG  ACTGGGCAGA  TGAACATGGC  ATCGTGGTGA  TTGATGAAAC  2520

TGCTGCTGTC  GGCTTTAACC  TCTCTTTAGG  CATTGGTTTC  GAAGCGGGCA  ACAAGCCGAA  2580

AGAACTGTAC  AGCGAAGAGG  CAGTCAACGG  GGAAACTCAG  CAAGCGCACT  TACAGGCGAT  2640

TAAAGAGCTG  ATAGCGCGTG  ACAAAAACCA  CCCAAGCGTG  GTGATGTGGA  GTATTGCCAA  2700

CGAACCGGAT  ACCCGTCCGC  AAGTGCACGG  GAATATTTCG  CCACTGGCGG  AAGCAACGCG  2760

TAAACTCGAC  CCGACGCGTC  CGATCACCTG  CGTCAATGTA  ATGTTCTGCG  ACGCTCACAC  2820

CGATACCATC  AGCGATCTCT  TTGATGTGCT  GTGCCTGAAC  CGTTATTACG  GATGGTATGT  2880

CCAAAGCGGC  GATTTGGAAA  CGGCAGAGAA  GGTACTGGAA  AAAGAACTTC  TGGCCTGGCA  2940

GGAGAAACTG  CATCAGCCGA  TTATCATCAC  CGAATACGGC  GTGGATACGT  TAGCCGGGCT  3000

GCACTCAATG  TACACCGACA  TGTGGAGTGA  AGAGTATCAG  TGTGCATGGC  TGGATATGTA  3060

TCACCGCGTC  TTTGATCGCG  TCAGCGCCGT  CGTCGGTGAA  CAGGTATGGA  ATTTCGCCGA  3120

TTTTGCGACC  TCGCAAGGCA  TATTGCGCGT  TGGCGGTAAC  AAGAAAGGGA  TCTTCACTCG  3180

CGACCGCAAA  CCGAAGTCGG  CGGCTTTTCT  GCTGCAAAAA  CGCTGGACTG  GCATGAACTT  3240

CGGTGAAAAA  CCGCAGCAGG  GAGGCAAACA  ATGAATCAAC  AACTCTCCTG  GCGCACCATC  3300

GTCGGCTACA  GCCTCGGTGA  CGTCGCCAAT  AACTTCGCCT  TCGCAATGGG  GGCGCTCTTC  3360

CTGTTGAGTT  ACTACACCGA  CGTCGCTGGC  GTCGGTGCCG  CTGCGGCGGG  CACCATGCTG  3420

TTACTGGTGC  GGGTATTCGA  TGCCTTCGCC  GACGTCTTTG  CCGGACGAGT  GGTGGACAGT  3480

GTGAATACCC  GCTGGGGAAA  ATTCCGCCCG  TTTTTACTCT  TCGGTACTGC  GCCGTTAATG  3540

ATCTTCAGCG  TGCTGGTATT  CTGGGTGCCG  ACCGACTGGA  GCCATGGTAG  CAAAGTGGTG  3600

TATGCATATT  TGACCTACAT  GGGCCTCGGG  CTTTGCTACA  GCCTGGTGAA  TATTCCTTAT  3660

GGTTCACTTG  CTACCGCGAT  GACCCAACAA  CCACAATCCC  GCGCCCGTCT  GGGCGCGGCT  3720

CGTGGGATTG  CCGCTTCATT  GACCTTTGTC  TGCCTGGCAT  TTCTGATAGG  ACCGAGCATT  3780

AAGAACTCCA  GCCCGGAAGA  GATGGTGTCG  GTATACCATT  TCTGGACAAT  TGTGCTGGCG  3840

ATTGCCGGAA  TGGTGCTTTA  CTTCATCTGC  TTCAAATCGA  CGCGTGAGAA  TGTGGTACGT  3900

ATCGTTGCGC  AGCCGTCATT  GAATATCAGT  CTGCAAACCC  TGAAACGGAA  TCGCCCGCTG  3960

TTTATGTTGT  GCATCGGTGC  GCTGTGTGTG  CTGATTTCGA  CCTTTGCGGT  CAGCGCCTCG  4020

TCGTTGTTCT  ACGTGCGCTA  TGTGTTAAAT  GATACCGGGC  TGTTCACTGT  GCTGGTACTG  4080

GTGCAAAACC  TGGTTGGTAC  TGTGGCATCG  GCACCGCTGG  TGCCGGGGAT  GGTCGCGAGG  4140

ATCGGTAAAA  AGAATACCTT  CCTGATTGGC  GCTTTGCTGG  GAACCTGCGG  TTATCTGCTG  4200

TTCTTCTGGG  TTTCCGTCTG  GTCACTGCCG  GTGGCGTTGG  TTGCGTTGGC  CATCGCTTCA  4260

ATTGGTCAGG  GCGTTACCAT  GACCGTGATG  TGGGCGCTGG  AAGCTGATAC  CGTAGAATAC  4320

GGTGAATACC  TGACCGGCGT  GCGAATTGAA  GGGCTCACCT  ATTCACTATT  CTCATTTACC  4380

CGTAAATGCG  GTCAGGCAAT  CGGAGGTTCA  ATTCCTGCCT  TTATTTTGGG  GTTAAGCGGA  4440

TATATCGCCA  ATCAGGTGCA  AACGCCGGAA  GTTATTATGG  CATCCGCAC  ATCAATTGCC  4500

TTAGTACCTT  GCGGATTTAT  GCTACTGGCA  TTCGTTATTA  TCTGGTTTTA  TCCGCTCACG  4560

GATAAAAAAT  TCAAAGAAAT  CGTGGTTGAA  ATTGATAATC  GTAAAAAGT   GCAGCAGCAA  4620

TTAATCAGCG  ATATCACTAA  TTAATATTCA  ATAAAAATAA  TCAGAACATC  AAAGGTGCAA  4680

CTATGAGAAA  AATAGTGGCC  ATGGCCGTTA  TTTGCCTGAC  GGCTGCCTCT  GGCCTTACCT  4740

CTGCTTATGC  GGCGCAACTG  GCTGACGATG  AAGCGGGACT  ACGCATCAGA  CTGAAAAACG  4800

AATTGCGCAG  GGCGGATAAG  CCCAGTGCTG  GCGCGGGAAG  AGATATTTAC  GCATGGGTAC  4860
```

| | | | | | | |
|---|---|---|---|---|---|---|
| AGGGAGGATT | GCTCGATTTC | AATAGTGGTT | ATTATTCCAA | TATTATTGGC | GTTGAAGGCG | 4920 |
| GGGCGTATTA | TGTTTATAAA | TTAGGTGCTC | GTGCTGATAT | GAGTACCCGG | TGGTATCTTG | 4980 |
| ATGGTGATAA | AAGTTTTGCT | TTGCCCGGGG | CAGTAAAAAT | AAAACCCAGT | GAAAATAGCC | 5040 |
| TGCTTAAATT | AGGTCGCTTC | GGGACGGATT | ATAGTTATGG | TAGCTTACCT | TATCGTATTC | 5100 |
| CGTTAATGGC | TGGCAGTTCG | CAACGTACAT | TACCGACAGT | TTCTGAAGGA | GCATTAGGTT | 5160 |
| ATTGGGCTTT | AACACCAAAT | ATTGATCTGT | GGGGAATGTG | GCGTTCACGA | GTATTTTTAT | 5220 |
| GGACTGATTC | AACAACCGGT | ATTCGTGATG | AAGGGGTGTA | TAACAGCCAG | ACGGGAAAAT | 5280 |
| ACGATAAACA | TCGCGCACGT | TCTTTTTTAG | CCGCCAGTTG | GCATGATGAT | ACCAGTCGCT | 5340 |
| ATTCTCTGGG | GGCATCGGTA | CAGAAAGATG | TTTCCAATCA | GATACAAAGT | ATTCTCGAGA | 5400 |
| AAAGCATACC | GCTCGACCCG | AATTATACGT | TGAAAGGGGA | GTTGCTCGGC | TTTTACGCGC | 5460 |
| AGCTCGAAGG | TTTAAGTCGT | AATACCAGCC | AGCCCAATGA | AACGGCGTTG | GTTAGTGGAC | 5520 |
| AATTGACCTG | GAATGCGCCG | TGGGGAAGTG | TATTTGGCAG | TGGTGGTTAT | TTGCGCCATG | 5580 |
| CAATGAATGG | TGCCGTGGTG | GATACCGACA | TTGGCTATCC | CTTTTCATTA | AGTCTTGATC | 5640 |
| GTAACCGTGA | AGGAATGCAG | TCCTGGCAAT | TGGGCGTCAA | CTATCGTTTA | ACGCCGCAAT | 5700 |
| TTACGCTGAC | ATTTGCACCG | ATTGTGACTC | GCGGCTATGA | ATCCAGTAAA | CGAGATGTGC | 5760 |
| GGATTGAAGG | CACGGGTATC | TTAGGTGGTA | TGAACTATCG | GGTCAGCGAA | GGGCCGTTAC | 5820 |
| AAGGGATGAA | TTTCTTTCTT | GCTGCCGATA | AGGGCGGGA | AAAGCGCGAT | GGCAGTACGC | 5880 |
| TGGGCGATCG | CCTGAATTAC | TGGGATGTGA | AAATGAGTAT | TCAGTATGAC | TTTATGCTGA | 5940 |
| AGTAAAAAAT | AACGCCGGAG | AGAAAAATCT | CCGGCGTTTC | AGATTGTTGA | CAAAGTGCCG | 6000 |
| TTTTTTATGC | CGGATGCGGC | TAAACGCCTT | ATCCAGCCTA | CAAAAACTCA | TAAATTCAAA | 6060 |
| GTGTTGCAGG | AAAAGGTAGG | CCTGATAAGC | GTAGCGCATC | AGGCAATCTC | TGGTTTGTTT | 6120 |
| TCAGATGAAA | ACGCCGGAGT | GAAAATTCTC | CGGCGTTTTG | GCCGTGAATT | ACTGCTGCGG | 6180 |
| AATTGCCGGT | ACAGCCGGAA | CGTTAAGAGC | TGGCATCGCA | AACATGCCAA | CAAAATCTTC | 6240 |
| TAACGACATT | TTCTGCCCAT | TTAACGTTAT | CTGACCGTTA | GCATATTGCA | GGCTGGTGGT | 6300 |
| GATGGTATTG | TCCTGCAAGG | TGGTCAGACG | GAACATCTGC | CCCATTGCTG | ATGCACCTTC | 6360 |
| AACTTGCTGT | TTCGCCAGTT | TTTTCGCTTG | ATCTTCCTGA | TAACCTTCCT | CGCTACCTGA | 6420 |
| GTCATAAACT | CAGTTGCCAT | ATCCACCGGA | ATGGTCAGTT | TCGCATCCAG | AGATTTAACC | 6480 |
| GAACGATCTA | CTTCCTGCGC | CAGCGTTTGC | GGCGCTTCTT | TAGTCGTTGC | CGGATCTTTC | 6540 |
| AGGAACAGCG | ACAGATTCAG | GGCACTTTCA | CCCTGACTGT | TTTTCCAGCT | TAGCGGCGCG | 6600 |
| ATAGTAATCA | CCGGATCGCC | TTTCAGCATC | AGCGGCAGGG | CGCTAAAGAA | GGCTTCCGTC | 6660 |
| ACTTTCTCCT | GATAAAGTTC | GGGGTTGTTG | GCAATTTCTG | GCTGTCGCGA | CAGCGCCTGA | 6720 |
| GTTTGCGCGT | TATATTGCTG | GCTAAACTGA | TGCCAGGCTT | CACCATCAAT | CTGGCCGACT | 6780 |
| TTTAAAGTCA | GCTTGCCGCT | GCCCAGATCC | TGATTCTGTA | CCTTCAGGCT | GTTTAGCGAG | 6840 |
| TAATCCAGTT | GGCTATTGAT | CGTTTACCG | TCATTGACCA | GATCCGATTT | ACCGCTGATC | 6900 |
| TCCATGCCTT | CCAGCAGTGC | CAGTTCTTTG | CCTTCCACTG | AAATGGTCAT | TTTTTCCAGT | 6960 |
| GACAGTTTTT | GATTTCCTAC | ACGCTCACCA | AAACTTGCCA | GCGTGCTGGA | ACCGTCGGTT | 7020 |
| TTCAGATTAT | TAAAGGTCAA | CTGCACTTTC | TGGTTGTATT | CGTTAACTGC | GTCTATCCGA | 7080 |
| ACCACTTTGC | GCCTCCCCGG | AAAGGGAGAT | GGCTTGCGT | CTCTGTCAGC | ATTTAACTGG | 7140 |
| AACTCGCCGC | CGCTAAAGGC | GACTTTTTCA | TCCTTTTGCT | CGTAATTCAG | TGGCTTGAGC | 7200 |
| GAAATATCGG | AACTGGAATC | ACCGCTGTAA | CCAATGCGCG | AGTTAATCTC | AAAAGGCGTT | 7260 |

```
TCACCTTTTG CCATATCAAA CAGTGGTTTG CTTACTTCGT TATTAACCAG CGTGGTTTGA      7320

ATTGATGCCA TCGACGGGAT CAGGTTCAGT TTTTTAAGCT GGGCAAGCGG GAAGGGACCA      7380

TGATCAACCG ATTCGTTGAA GATGACGCTC TGACCGCTTT TAATCCACGG ATTTTCTTTC      7440

CCGGCAATGG GTTTCACCAA CAGTTGCAAC TGGCTGCTGA ATACGCCGCG ATGATAGTTT      7500

TGATAACTCA CTTCCAGGTT GGATTCAGGA GCTGTCAGTT TGAGTTGCGC GTTCGCCTGC      7560

GCGACCATGT CTTCGAGATG GGTTTCAATC TTCTTGCCTG TATACCATGC GCCGCCTGTC      7620

CAGACTACGC CTAGCGCAAC AATGACGCCT ACCGCTACCA GCGATTATT CATAATGATT       7680

ATCCATAAAA TGAAATCAGG CGGACTGGCC GCCTGAAGGT GTTATAAGCC TTTAATAAGC      7740

TT                                                                     7742
```

(2) INFORMATION FOR SEQ ID NO:5:

(i) SEQUENCE CHARACTERISTICS:
        (A) LENGTH: 602 amino acids
        (B) TYPE: amino acid
        (C) STRANDEDNESS: single
        (D) TOPOLOGY: linear (xi) SEQUENCE DESCRIPTION: SEQ ID NO:5:

```
Met Leu Arg Pro Val Glu Thr Pro Thr Arg Glu Ile Lys Lys Leu Asp
 1               5                  10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270
```

```
Ser Val Ala Val Lys Gly Glu Gln Phe Leu Ile Asn His Lys Pro Phe
    275             280                 285
Tyr Phe Thr Gly Phe Gly Arg His Glu Asp Ala Asp Leu Arg Gly Lys
    290             295                 300
Gly Phe Asp Asn Val Leu Met Val His Asp His Ala Leu Met Asp Trp
305             310              315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
            340             345                 350
Ala Ala Val Gly Phe Asn Leu Ser Leu Gly Ile Gly Phe Glu Ala Gly
        355             360              365
Asn Lys Pro Lys Glu Leu Tyr Ser Glu Glu Ala Val Asn Gly Glu Thr
    370             375                 380
Gln Gln Ala His Leu Gln Ala Ile Lys Glu Leu Ile Ala Arg Asp Lys
385             390             395                 400
Asn His Pro Ser Val Val Met Trp Ser Ile Ala Asn Glu Pro Asp Thr
                405             410                 415
Arg Pro Gln Val His Gly Asn Ile Ser Pro Leu Ala Glu Ala Thr Arg
            420             425                 430
Lys Leu Asp Pro Thr Arg Pro Ile Thr Cys Val Asn Val Met Phe Cys
        435             440                 445
Asp Ala His Thr Asp Thr Ile Ser Asp Leu Phe Asp Val Leu Cys Leu
        450             455                 460
Asn Arg Tyr Tyr Gly Trp Tyr Val Gln Ser Gly Asp Leu Glu Thr Ala
465             470                 475                 480
Glu Lys Val Leu Glu Lys Glu Leu Leu Ala Trp Gln Glu Lys Leu His
                485             490                 495
Gln Pro Ile Ile Ile Thr Glu Tyr Gly Val Asp Thr Leu Ala Gly Leu
            500             505                 510
His Ser Met Tyr Thr Asp Met Trp Ser Glu Glu Tyr Gln Cys Ala Trp
            515             520                 525
Leu Asp Met Tyr His Arg Val Phe Asp Arg Val Ser Ala Val Val Gly
    530             535                 540
Glu Gln Val Trp Asn Phe Ala Asp Phe Ala Thr Ser Gln Gly Ile Leu
545             550             555                 560
Arg Val Gly Gly Asn Lys Lys Gly Ile Phe Thr Arg Asp Arg Lys Pro
                565             570                 575
Lys Ser Ala Ala Phe Leu Leu Gln Lys Arg Trp Thr Gly Met Asn Phe
            580             585                 590
Gly Glu Lys Pro Gln Gln Gly Gly Lys Gln
            595             600
```

( 2 ) INFORMATION FOR SEQ ID NO:6:

( i ) SEQUENCE CHARACTERISTICS:
( A ) LENGTH: 457 amino acids
( B ) TYPE: amino acid
( C ) STRANDEDNESS: single
( D ) TOPOLOGY: linear ( x i ) SEQUENCE DESCRIPTION: SEQ ID NO:6:

```
Met Asn Gln Gln Leu Ser Trp Arg Thr Ile Val Gly Tyr Ser Leu Gly
1               5                   10                  15
Asp Val Ala Asn Asn Phe Ala Phe Ala Met Gly Ala Leu Phe Leu Leu
                20              25                  30
```

```
Ser  Tyr  Tyr  Thr  Asp  Val  Ala  Gly  Val  Gly  Ala  Ala  Ala  Ala  Gly  Thr
          35                      40                          45

Met  Leu  Leu  Leu  Val  Arg  Val  Phe  Asp  Ala  Phe  Ala  Asp  Val  Phe  Ala
 50                      55                      60

Gly  Arg  Val  Val  Asp  Ser  Val  Asn  Thr  Arg  Trp  Gly  Lys  Phe  Arg  Pro
 65                      70                      75                           80

Phe  Leu  Leu  Phe  Gly  Thr  Ala  Pro  Leu  Met  Ile  Phe  Ser  Val  Leu  Val
               85                      90                          95

Phe  Trp  Val  Pro  Thr  Asp  Trp  Ser  His  Gly  Ser  Lys  Val  Val  Tyr  Ala
              100                     105                         110

Tyr  Leu  Thr  Tyr  Met  Gly  Leu  Gly  Leu  Cys  Tyr  Ser  Leu  Val  Asn  Ile
          115                     120                         125

Pro  Tyr  Gly  Ser  Leu  Ala  Thr  Ala  Met  Thr  Gln  Gln  Pro  Gln  Ser  Arg
         130                     135                         140

Ala  Arg  Leu  Gly  Ala  Ala  Arg  Gly  Ile  Ala  Ala  Ser  Leu  Thr  Phe  Val
145                          150                     155                      160

Cys  Leu  Ala  Phe  Leu  Ile  Gly  Pro  Ser  Ile  Lys  Asn  Ser  Ser  Pro  Glu
               165                     170                         175

Glu  Met  Val  Ser  Val  Tyr  His  Phe  Trp  Thr  Ile  Val  Leu  Ala  Ile  Ala
              180                     185                         190

Gly  Met  Val  Leu  Tyr  Phe  Ile  Cys  Phe  Lys  Ser  Thr  Arg  Glu  Asn  Val
              195                     200                         205

Val  Arg  Ile  Val  Ala  Gln  Pro  Ser  Leu  Asn  Ile  Ser  Leu  Gln  Thr  Leu
         210                     215                         220

Lys  Arg  Asn  Arg  Pro  Leu  Phe  Met  Leu  Cys  Ile  Gly  Ala  Leu  Cys  Val
225                          230                     235                      240

Leu  Ile  Ser  Thr  Phe  Ala  Val  Ser  Ala  Ser  Ser  Leu  Phe  Tyr  Val  Arg
              245                     250                         255

Tyr  Val  Leu  Asn  Asp  Thr  Gly  Leu  Phe  Thr  Val  Leu  Val  Leu  Val  Gln
              260                     265                         270

Asn  Leu  Val  Gly  Thr  Val  Ala  Ser  Ala  Pro  Leu  Val  Pro  Gly  Met  Val
              275                     280                         285

Ala  Arg  Ile  Gly  Lys  Lys  Asn  Thr  Phe  Leu  Ile  Gly  Ala  Leu  Leu  Gly
290                          295                     300

Thr  Cys  Gly  Tyr  Leu  Leu  Phe  Phe  Trp  Val  Ser  Val  Trp  Ser  Leu  Pro
305                          310                     315                      320

Val  Ala  Leu  Val  Ala  Leu  Ala  Ile  Ala  Ser  Ile  Gly  Gln  Gly  Val  Thr
              325                     330                         335

Met  Thr  Val  Met  Trp  Ala  Leu  Glu  Ala  Asp  Thr  Val  Glu  Tyr  Gly  Glu
              340                     345                         350

Tyr  Leu  Thr  Gly  Val  Arg  Ile  Glu  Gly  Leu  Thr  Tyr  Ser  Leu  Phe  Ser
          355                     360                         365

Phe  Thr  Arg  Lys  Cys  Gly  Gln  Ala  Ile  Gly  Gly  Ser  Ile  Pro  Ala  Phe
          370                     375                         380

Ile  Leu  Gly  Leu  Ser  Gly  Tyr  Ile  Ala  Asn  Gln  Val  Gln  Thr  Pro  Glu
385                          390                     395                      400

Val  Ile  Met  Gly  Ile  Arg  Thr  Ser  Ile  Ala  Leu  Val  Pro  Cys  Gly  Phe
                   405                     410                         415

Met  Leu  Leu  Ala  Phe  Val  Ile  Ile  Trp  Phe  Tyr  Pro  Leu  Thr  Asp  Lys
               420                     425                         430

Lys  Phe  Lys  Glu  Ile  Val  Val  Glu  Ile  Asp  Asn  Arg  Lys  Lys  Val  Gln
          435                     440                         445

Gln  Gln  Leu  Ile  Ser  Asp  Ile  Thr  Asn
```

450 455

(2) INFORMATION FOR SEQ ID NO:7:

(i) SEQUENCE CHARACTERISTICS:
        (A) LENGTH: 416 amino acids
        (B) TYPE: amino acid
        (C) STRANDEDNESS: single
        (D) TOPOLOGY: linear (xi) SEQUENCE DESCRIPTION: SEQ ID NO:7:

```
Met Ala Met Ala Val Ile Cys Leu Thr Ala Ala Ser Gly Leu Thr Ser
 1               5                  10                  15

Ala Tyr Ala Ala Gln Leu Ala Asp Asp Glu Ala Gly Leu Arg Ile Arg
                20                  25                  30

Leu Lys Asn Glu Leu Arg Arg Ala Asp Lys Pro Ser Ala Gly Ala Gly
                35                  40                  45

Arg Asp Ile Tyr Ala Trp Val Gln Gly Gly Leu Leu Asp Phe Asn Ser
        50                  55                  60

Gly Tyr Tyr Ser Asn Ile Ile Gly Val Glu Gly Gly Ala Tyr Tyr Val
 65                  70                  75                  80

Tyr Lys Leu Gly Ala Arg Ala Asp Met Ser Thr Arg Trp Tyr Leu Asp
                85                  90                  95

Gly Asp Lys Ser Phe Ala Leu Pro Gly Ala Val Lys Ile Lys Pro Ser
               100                 105                 110

Glu Asn Ser Leu Leu Lys Leu Gly Arg Phe Gly Thr Asp Tyr Ser Tyr
               115                 120                 125

Gly Ser Leu Pro Tyr Arg Ile Pro Leu Met Ala Gly Ser Ser Gln Arg
       130                 135                 140

Thr Leu Pro Thr Val Ser Glu Gly Ala Leu Gly Tyr Trp Ala Leu Thr
145                 150                 155                 160

Pro Asn Ile Asp Leu Trp Gly Met Trp Arg Ser Arg Val Phe Leu Trp
                165                 170                 175

Thr Asp Ser Thr Thr Gly Ile Arg Asp Glu Gly Val Tyr Asn Ser Gln
               180                 185                 190

Thr Gly Lys Tyr Asp Lys His Arg Ala Arg Ser Phe Leu Ala Ala Ser
       195                 200                 205

Trp His Asp Asp Thr Ser Arg Tyr Ser Leu Gly Ala Ser Val Gln Lys
   210                 215                 220

Asp Val Ser Asn Gln Ile Gln Ser Ile Leu Glu Lys Ser Ile Pro Leu
225                 230                 235                 240

Asp Pro Asn Tyr Thr Leu Lys Gly Glu Leu Leu Gly Phe Tyr Ala Gln
                245                 250                 255

Leu Glu Gly Leu Ser Arg Asn Thr Ser Gln Pro Asn Glu Thr Ala Leu
                260                 265                 270

Val Ser Gly Gln Leu Thr Trp Asn Ala Pro Trp Gly Ser Val Phe Gly
       275                 280                 285

Ser Gly Gly Tyr Leu Arg His Ala Met Asn Gly Ala Val Val Asp Thr
   290                 295                 300

Asp Ile Gly Tyr Pro Phe Ser Leu Ser Leu Asp Arg Asn Arg Glu Gly
305                 310                 315                 320

Met Gln Ser Trp Gln Leu Gly Val Asn Tyr Arg Leu Thr Pro Gln Phe
                325                 330                 335

Thr Leu Thr Phe Ala Pro Ile Val Thr Arg Gly Tyr Glu Ser Ser Lys
       340                 345                 350

Arg Asp Val Arg Ile Glu Gly Thr Gly Ile Leu Gly Gly Met Asn Tyr
```

|     | 355 |     |     |     |     | 360 |     |     |     |     | 365 |     |     |     |
| --- | --- | --- | --- | --- | --- | --- | --- | --- | --- | --- | --- | --- | --- | --- |
| Arg | Val | Ser | Glu | Gly | Pro | Leu | Gln | Gly | Met | Asn | Phe | Leu | Ala | Ala |
|     | 370 |     |     |     |     | 375 |     |     |     |     | 380 |     |     |     |
| Asp | Lys | Gly | Arg | Glu | Lys | Arg | Asp | Gly | Ser | Thr | Leu | Gly | Asp | Arg | Leu |
| 385 |     |     |     |     | 390 |     |     |     |     | 395 |     |     |     | 400 |
| Asn | Tyr | Trp | Asp | Val | Lys | Met | Ser | Ile | Gln | Tyr | Asp | Phe | Met | Leu | Lys |
|     |     |     |     | 405 |     |     |     |     | 410 |     |     |     |     | 415 |

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGAGAATTCG AGGAGTCCAT CATGATGGAT AACATGCAGA CTGAAG     46

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCTGAATTCA AGCTTCAGGA TGCGGTTAAG ATACCGCC     38

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GACCAGGTTA CCATGGATAA CATGCAGACT GAAGCAC     37

( 2 ) INFORMATION FOR SEQ ID NO:11:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GACGTGATGG TGGCTAGCGG ATGCGGTTAA GATACCGCCA ATC     43

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GATCCACAGA ATTGGTTAAC TAATCAGATG     30

( 2 ) INFORMATION FOR SEQ ID NO:13:

( i ) SEQUENCE CHARACTERISTICS:

(A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:13:

GTGTCTTAAC CAATTGATTA GTCTACTAAT												30

(2) INFORMATION FOR SEQ ID NO:14:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (xi) SEQUENCE DESCRIPTION: SEQ ID NO:14:

GATCCGGCTA TTGGTTAACC AATTTCAG												28

(2) INFORMATION FOR SEQ ID NO:15:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (xi) SEQUENCE DESCRIPTION: SEQ ID NO:15:

GCCGATAACC AATTGGTTAA AGTCTAAT												28

(2) INFORMATION FOR SEQ ID NO:16:

(i) SEQUENCE CHARACTERISTICS:
                (A) LENGTH: 48 base pairs
                (B) TYPE: nucleic acid
                (C) STRANDEDNESS: single
                (D) TOPOLOGY: linear (xi) SEQUENCE DESCRIPTION: SEQ ID NO:16:

AATTCCGTTC CCAATACGCT CGAACGAACG TTCGGTTGCT TATTTTAG												48

(2) INFORMATION FOR SEQ ID NO:17:

(i) SEQUENCE CHARACTERISTICS:
                (A) LENGTH: 48 base pairs
                (B) TYPE: nucleic acid
                (C) STRANDEDNESS: single
                (D) TOPOLOGY: linear (xi) SEQUENCE DESCRIPTION: SEQ ID NO:17:

GGCAAGGGTT ATGCGAGCTT GCTTGCAAGC CAACGAATAA AATCCTAG												48

(2) INFORMATION FOR SEQ ID NO:18:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (xi) SEQUENCE DESCRIPTION: SEQ ID NO:18:

GATCCCATCG AACGTTCGAT GG												22

(2) INFORMATION FOR SEQ ID NO:19:

(i) SEQUENCE CHARACTERISTICS:
                (A) LENGTH: 22 base pairs
                (B) TYPE: nucleic acid ( C ) STRANDEDNESS: single
( D ) TOPOLOGY: linear ( x i ) SEQUENCE DESCRIPTION: SEQ ID NO:19:

GGTAGCTTGC AAGCTACCCT AG 22

GLUCURONIDE REPRESSORS AND USES THEREOF

CROSS-RELATED APPLICATIONS

The present application claims priority from U.S. Provisional application Ser. No. 60/020,621 filed Jun. 26, 1996, which application is incorporated herein by reference in its entirety.

TECHNICAL FIELD

The present invention relates generally to a repressor molecule for a glucuronidase operon and, more specifically, to amino acid and DNA sequences of a repressor and uses for a repressor protein.

BACKGROUND OF THE INVENTION

The natural habitat of *E. coli* is the gut, and the β-glucuronidase activity of *E. coli* plays a specific and very important role in its natural history. The gut is a rich source of glucuronic acid compounds, providing a carbon source that can be efficiently exploited by *E. coli*. Glucuronide substrates are taken up by *E. coli* via a specific transporter, the glucuronide permease (U.S. Pat. Nos. 5,288,463 and 5,432,081) and cleaved by β-glucuronidase. The glucuronic acid residue thus released is used as a carbon source.

In general, the aglycon component of the glucuronide substrate is not used by *E. coli* and passes back across the bacterial membrane into the gut to be reabsorbed into the bloodstream. This circulation of hydrophobic compounds resulting from the opposing processes of glucuronidation in the liver and deglucuronidation in the gut is termed enterohepatic circulation. This phenomenon is of great physiological importance because it means that, due in large part to the action of microbial β-glucuronidase, many compounds including endogenous steroid hormones and exogenously administered drugs are not eliminated from the body all at once. Rather, the levels of these compounds in the bloodstream oscillate due to this circulatory process. This process is of great significance in determining pharmaceutical dosages, and indeed some drugs are specifically administered as the glucuronide conjugate, relying on the action of β-glucuronidase to release the active aglycon (Draser and Hill, 1974).

β-glucuronidase is encoded by the gusA locus of *E. coli* (Novel and Novel, *Mol. Gen. Genet.* 120: 319–335, 1973). gusA (GUS) is one member of an operon, consisting of three protein-encoding genes. The second gene, gusB (PER), encodes a specific permease for β-glucuronides. The third gene, gusc (MOP), encodes an outer membrane protein of approximately 50 kDa that facilitates access of glucuronides to the permease located in the inner membrane. The principle repressor for the gus operon, gusR, maps immediately upstream of the operon.

β-glucuronidase activity is not constitutively expressed in *E. coli*; rather, transcription of the operon is regulated by several factors. The primary mechanism of control is induction by glucuronide substrates. This regulation is due to the action of the product of the gusR (formerly uidR) gene which encodes the repressor. gusR was mapped by deletion mutation analysis to the same region of the chromosome as gusA, lying upstream of gusA. GusR repression of β-glucuronidase activity has been shown by Northern analysis to be mediated by transcriptional regulation: RNA from uninduced cultures of *E. coli* does not hybridize to a gusA probe, in contrast to the strong hybridization observed to RNA extracted from cultures that had been induced with methyl β-D-glucuronide (Jefferson, DNA Transformation of *Caenorhabditis elegans:* Development and Application of a New Gene Fusion System. Ph.D. Dissertation, University of Colorado, Boulder, Colo., 1985). Presumably, therefore, GusR represses gusA transcription by binding to gusA operator sequences, thereby preventing transcription. This repression would then be relieved when a glucuronide substrate binds to the repressor and inactivates it.

The present invention provides gene and protein sequences of glucuronide repressors and use of the repressor for controlling gene expression and detecting glucuronides, while providing other related advantages.

SUMMARY OF THE INVENTION

This invention generally provides isolated nucleic acid molecules encoding a glucuronide repressor. In particular, a nucleotide and amino acid sequence of the *E. coli* glucuronide repressor (gusR) are provided. In preferred embodiments, the nucleotide sequence of the repressor is presented in SEQ. ID. NO: 1 or a variant thereof. In certain embodiments, nucleic acid molecules that hybridize to gusR are provided. Nucleic acid sequences that encode glucuronide binding site of a glucuronide repressor are presented.

In another aspect, this invention provides a glucuronide repressor protein that binds to a glucuronide operator and that binds to a glucuronide, wherein the binding to the operator is inversely dependent on glucuronide binding. In certain preferred embodiments the repressor comprises the sequence presented in SEQ. ID NO: 2 or a variant thereof. In other preferred embodiments, the repressor comprises a fusion protein of a glucuronide binding site or domain and a nucleotide-binding domain.

In yet other aspects, methods for isolating a glucuronide are provided, comprising (a) contacting a glucuronide binding domain from a glucuronide with a sample containing a glucuronide, wherein the glucuronide binds to the repressor protein; and (b) eluting the glucuronide from the repressor.

Other aspects provide methods for determining the presence or detecting the presence of a glucuronide in a sample, comprising (a) binding a repressor protein to a nucleic acid molecule comprising a glucuronide operator sequence to form a complex; (b) contacting the complex with a sample containing a glucuronide, wherein the glucuronide binds to the repressor protein causing release of the protein from the nucleic acid molecule; and (c) detecting release of the protein.

In other aspects, methods are provided for controlling gene expression of a transgene, comprising (a) transfecting or transforming a cell with a nucleic acid molecule comprising a nucleotide sequence encoding the repressor protein, a glucuronide operator sequence, and a transgene, wherein the operator is operably linked to the transgene; and (b) contacting the cell with a glucuronide that binds to the repressor protein; wherein the glucuronide causes the repressor protein to release from the operator sequence, thereby allowing expression of the transgene.

In yet other aspects, methods are provided for identifying a vertebrate glucuronide transport protein, comprising doubly transfecting a host cell lacking transport activity with a reporter gene under control of a glucuronide repressor and an expression library constructed from vertebrate RNA, and screening for expression of the reporter gene in the presence of a glucuronide.

These and other aspects of the present invention will become evident upon reference to the following detailed description and attached drawings. In addition, various references are set forth herein which describe in more detail certain procedures or compositions (e.g., plasmids, etc.), and are incorporated by reference in their entirety.

DETAILED DESCRIPTION OF THE INVENTION

Figure 1:
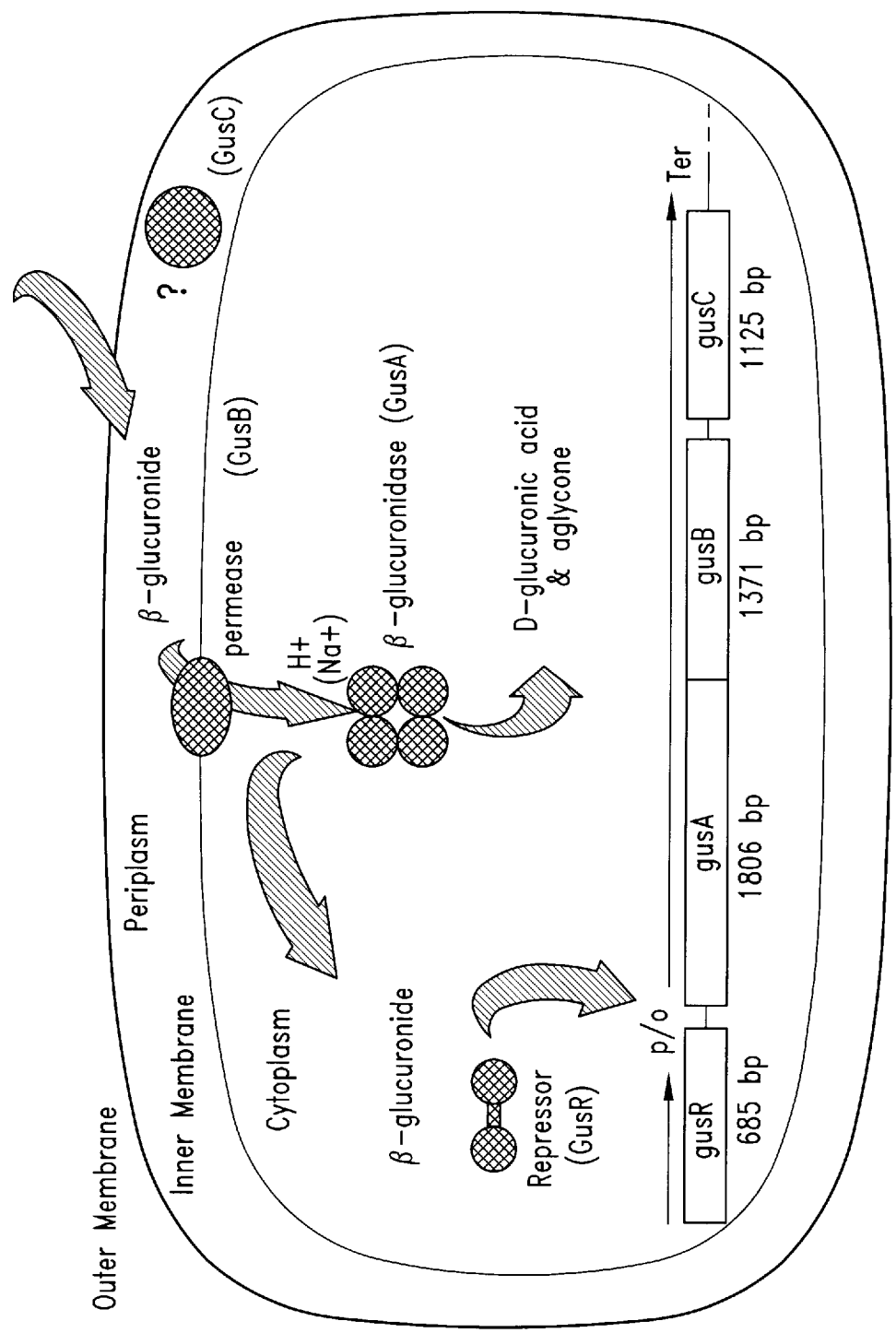
FIG. 1 is a drawing depicting the gus operon of *E. coli* and the activity of the gus proteins on a β-glucuronide.

Prior to setting forth the invention, it may be helpful to an understanding thereof to set forth definitions of certain terms that will be used hereinafter.

As used herein, "glucuronide" or "β-glucuronide" refers to any aglycon conjugated in a hemiacetal linkage, typically through the hydroxyl group, to the C1 of a free D-glucuronic acid in the β configuration. Glucuronides are generally very water soluble, due to the ionizable carboxylic acid group at the 6-carbon position in the glycon. Most aromatic and aliphatic glucuronides are remarkably stable relative to other types of glycoside conjugates, which may be due to the inductive effect of the carbonyl group at C-6 on the hemiacetal linkage at C-1. For example, colorigenic and fluorogenic substrates, such as p-nitrophenyl β-D-glucuronide, and 4-methylumbelliferyl β-D-glucuronide, are much more stable in aqueous solution than the corresponding β-D-galactosides or β-D-glucosides, making background due to spontaneous hydrolysis much less of a problem. Many β-glucuronides can be prepared free of other contaminating glycosides by vigorous acid hydrolysis, which cleaves glucosides, galactosides and other glycosides, but leaves most glucuronides intact. For example, complex carbohydrate polymers such as gum arabic can be reduced to a collection of monosaccharide components, and the single β-glucuronyl disaccharide aldobiuronic acid, simply by boiling gum arabic in sulfuric acid overnight.

β-glucuronides consist of virtually any compound linked to the 1-position of glucuronic acid as a beta anomer, and are typically, though by no means exclusively, found as the —O-glycoside. β-glucuronides are produced naturally through the action of UDP-glucuronyl transferase in many cells and tissues by most vertebrates as a part of the process of solubilizing, detoxifying, and mobilizing both natural and xenobiotic compounds, and thus directing them to sites of excretion or activity through the circulatory system. *E. coli* is able to cleave such glucuronides into their constituent molecules and use the glucuronic acid as an energy source through metabolism by the hexuronide-hexuronate pathway.

β-glucuronides in polysaccharide form are common in nature, most abundantly in vertebrates, where they are major constituents of connective and lubricative tissues (e.g., chondroitan sulfate of cartilage, and hyaluronic acid, which is the principle constituent of synovial fluid and mucus) in polymeric form with other sugars such as N-acetylglucosamine. β-glucuronides are relatively uncommon in plants. However, some plant gums and mucilages produced by wounded trees, notably gum arabic from *Acacia senegal*, do contain significant amounts of β-glucuronides in polymeric form, although rarely if ever as terminal residues that would serve as GUS substrates. Glucuronides and galacturonides found in plant cell wall components (such as pectin) are generally in the alpha configuration, and are frequently substituted as the 4-O-methyl ether; hence, these are not substrates for β-glucuronidase.

Within the context of this invention, certain β-glucuronide derivatives are used. Such β-glucuronide derivatives have the formula (1):

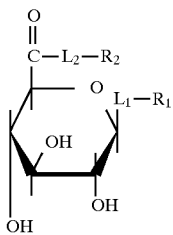

(1)

wherein $R_1$ is an aglycon moiety, $R_2$ is a hydrophobic moiety, and $L_1$ and $L_2$ are independently selected from linking groups. Preferred linking groups are independently selected from a direct bond, —O—, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—, where $R_3$ is H or a $C_1$–$C_{22}$ hydrocarbon group.

In a first embodiment: $R_1$ is an aglycon moiety; $L_1$ is selected from a direct bond, —O—, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—; $R_2$ is a hydrophobic moiety; $L_2$ is selected from a direct bond, —O—, —OC(=O)—, —C(=O)—, —N(R$_3$)—, —N(R$_3$)C(=O)—, and —S—; and $R_3$ is H or a $C_1$–$C_{22}$ hydrocarbon group.

In a preferred first embodiment: $R_1$ is an aglycon moiety; $L_1$ is selected from a direct bond, —O—, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—; $R_2$ is a lipid (—CH$_2$—CH(OC(=O)R$_3$)—CH$_2$(OC(=O)R$_3$) or a $C_1$–$C_{22}$ hydrocarbon group; $L_2$ is selected from a direct bond, —O—, —OC(=O)—, —C(=O)—, —N(R$_3$)—, —N(R$_3$)C(=O)—, and —S—; and $R_3$ is H or a $C_1$–$C_{22}$ hydrocarbon group.

In a more preferred first embodiment: $R_1$ is an aglycone moiety; $L_1$ is selected from a direct bond, —O—, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—; $R_2$ is selected from $C_1$–$C_{22}$alkyl, $C_6$–$C_{22}$aryl, $C_3$–$C_{22}$cycloalkyl, $C_7$–$C_{22}$arylalkyl, $C_7$–$C_{22}$alkylaryl and unsaturated derivatives thereof; $L_2$ is selected from a direct bond, —O—, and —N(R$_3$)—; and $R_3$ is H.

In a second embodiment: $R_1$ is an aglycone moiety; $L_1$ is a non-cleavable linkage selected from a direct bond, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—; $R_2$ is a hydrophobic group; $L_2$ is selected from a direct bond, —O—, —OC(=O)—, —C(=O)—, —N(R$_3$) —, —NHC(=O)—, and —S—; and $R_3$ is H or a $C_1$–$C_{22}$ hydrocarbon group.

In a preferred second embodiment: $R_1$ is a fluorogenic or chromogenic moiety; $L_1$ is a non-cleavable linkage selected from a direct bond, —OC(=O)—, —C(=O)O—, —C(=O)—, —CH(OR$_3$)—, —N(R$_3$)—, —N(R$_3$)C(=O) —, —C(=O)N(R$_3$)—, —N(R$_3$)C(=O)O—, —OC(=O)N (R$_3$)—, —S—, and —SS—; $R_2$ is a hydrophobic group; $L_2$ is selected from a direct bond, —O—, —OC(=O)—, —C(=O)—, —N(R$_3$)—, —NHC(=O)—, and —S—; and $R_3$ is H or a $C_1$–$C_{22}$ hydrocarbon group.

In a more preferred second embodiment: $R_1$ is a fluorogenic moiety selected from 4-methylumbelliferone, 3-cyano-4-methylumbelliferone, 4-trifluoromethylumbeliferone, fluorescein, 3-O-methylfluorescein and resorufin, or a chomrogenic moiety selected from 5-bromo-4-chloro-3-indoxyl, naphthol ASBI, phenolphthalein and p-nitrophenol; $L_1$ is selected from a direct bond, —N(R$_3$)—, and —S—; $R_2$ is a hydrophobic group; $L_2$ is selected from a direct bond, —O—, —OC(=O) —, —C(=O)—, —N(R$_3$)—, —NHC(=O)—, and —S—; and $R_3$ is H.

In a third embodiment: $R_1$ is an aglycon moiety; $L_1$ is a non-cleavable linkage selected from a direct bond, —OC(=O)—, —C(=O)O—, —C(=O)—, —CH(OR$_3$)—, —N(R$_3$)—, —N(R$_3$)C(=O)—, —C(=O)N(R$_3$)—, —N(R$_3$)C(=O)O—, —OC(=O)N(R$_3$)—, —S—, and —SS—; $R_2$ is a hydrophobic group; $L_2$ is selected from a direct bond, —O—, —OC(=O)—, —C(=O)—, —N(R$_3$) —, —NHC(=O)—, and —S—; and $R_3$ is H or a $C_1$–$C_{22}$ hydrocarbon group.

In a preferred third embodiment: $R_1$ is a fluorogenic or a chomrogenic moiety; $L_1$ is selected from a direct bond, —N(R$_3$)—, and —S—; $R_2$ is a lipid (—CH$_2$—CH(OC(=O) R$_3$)—CH$_2$(OC(=O)R$_3$) or a $C_1$–$C_{22}$ hydrocarbon group; $L_2$ is selected from a direct bond, —O—, and —N(R$_3$)—; and $R_3$ is H.

In a more preferred third embodiment: $R_1$ is a fluorogenic moiety selected from 4-methylumbelliferone, 3-cyano-4-methylumbelliferone, 4-trifluoromethylumbeliferone, fluorescein, 3-O-methylfluorescein and resorufin, or a chomrogenic moiety selected from 5-bromo-4-chloro-3-indoxyl, naphthol ASBI, phenolphthalein and p-nitrophenol; $L_1$ is selected from a direct bond, —N(R$_3$)—, and —S—; $R_2$ is selected from $C_1$–$C_{22}$alkyl, $C_6$–$C_{22}$aryl, $C_3$–$C_{22}$cycloalkyl, $C_7$–$C_{22}$arylalkyl, $C$–$C_{22}$alkylaryl and unsaturated derivatives thereof; $L_2$ is selected from a direct bond, —O—, and —N(R$_3$)—; and $R_3$ is H.

Compounds of formula (1) may be prepared by methodology known in the art. The compound of formula (1) wherein —$L_1$—$R_1$ and —$L_2$—$R_2$ are both —OH is known as glucuronic acid, and is commercially available from many sources. Also commercially available are some glucuronic acid derivatives wherein $R_1$ is a fluorogenic or chromogenic moiety. In order to provide compounds of formula (1) wherein —L$_2$—R$_2$ is other than —OH, the parent glucuronic acid may be esterified with an alcohol R$_2$—OH (to provide compounds wherein L$_2$ is oxygen), or reacted with an amine R$_2$—N(R$_3$)H. to provide amide compounds (L$_2$ is N(R$_3$)). Other derivatives may be prepared by procedures known in the art. See, e.g., Advanced Organic Chemistry (3rd edition) by J. March (McGraw-Hill Book Company). In some instances, the hydroxyl groups of the pyran ring in formula (1) may need to be protected, but this may be accomplished by known synthetic methodology. See, e.g., Greene, "Protective Groups in Organic Chemistry", John Wiley & Sons, New York N.Y. (1981).

As used herein, a "glucuronide operon" or a "GUS operon" refers to the concert of enzymes involved in transporting and cleaving β-glucuronides and the regulatory sequences. In E. coli, the operon comprises a repressor (gusR), a promoter/operator sequence, β-glucuronidase (gusA or GUS), β-glucuronide permease (gusB), and a membrane protein (gusC) (see, FIG. 1). Glucuronide operons or the vertebrate equivalent are found in most vertebrates and many mollusks (Levvy and Conchie, in Glucuronic Acid, Free and Combined, Dutton, G. J., ed. Academic Press, New York, 301, 1966). In contrast, glucuronide operons are largely, if not completely, absent from higher plants, mosses, ferns, insects, fungi, molds, and most bacterial genera, E. coil and Shigella being exceptions.

As used herein, a "glucuronide repressor" refers to a protein that has at least two interacting domains, one that binds a specific DNA sequence, and the other that binds a β-glucuronide or β-glucuronide derivative, such that the DNA binding is dependent upon β-glucuronide (or derivative) binding. The interaction may cause the protein to release from the glucuronide operator, as for a classical bacterial repressor, or bind to the operator as for a typical eukaryotic transcriptional activator. In addition, the repressor may have a third domain that allows dimerization of the protein. As noted above, most vertebrates and some mollusks have β-glucuronidase activity. The bacterial species, E. coil and Shigella, have a glucuronide repressor. In addition to referring to a glucuronide repressor from different species, glucuronide repressor also encompasses variants, including alleles, thereof. For certain embodiments, a variant, including an allele, must bind a β-glucuronide. For other embodiments, a variant must bind a glucuronide operator sequence. A variant may be a portion of the repressor and/or contain amino acid substitutions, insertions, and deletions. A variant may also be sufficiently similar in nucleotide sequence to hybridize to the native sequence.

As used herein, a "glucuronide operator" or "glucuronide operator sequence" refers to the specific nucleotide sequence bound by a glucuronide repressor. For example, the region containing the glucuronide operator sequence in E. coli is shown in SEQ ID NO: 3. More precise mapping of the operator site is discussed below and is presented in FIG. 18. The operator sequence may have nucleotide changes from native sequence as long as the repressor binds. Some changes may cause increased affinity of the repressor, some may cause decreased affinity. In general, increased affinity is preferred within the context of this invention.

Figure 2:
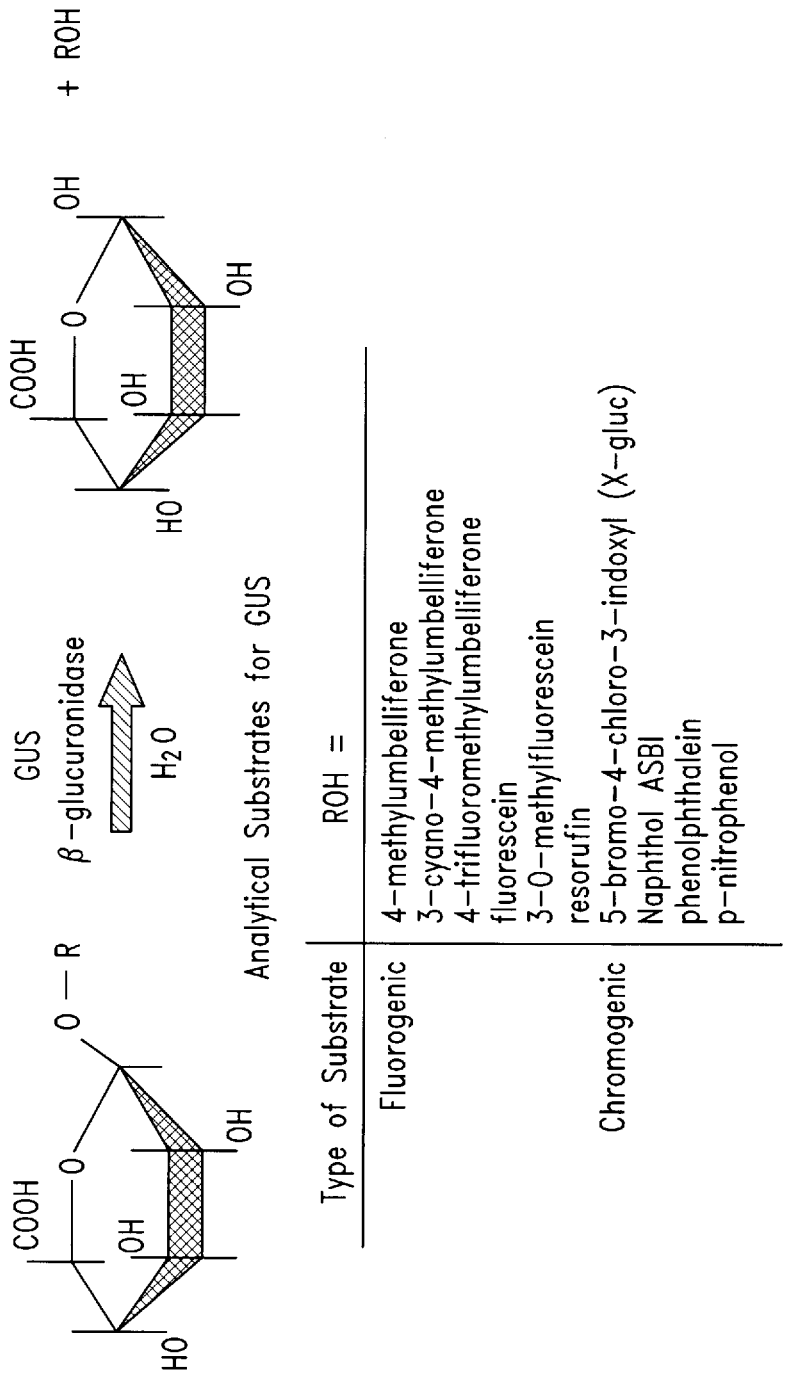
FIG. 2 shows the reaction catalyzed by β-glucuronidase and examples of various substrates useful for detection of GUS activity.

As used herein, "β-glucuronidase" refers to an enzyme that catalyzes the hydrolysis of β-glucuronides and derivatives. Almost any β-D-glucuronide serves as a substrate. For assays to detect β-glucuronidase activity, fluorogenic or chromogenic substrates are preferred. Such substrates include, but are not limited to, p-nitrophenyl β-D-glucuronide and 4-methylumbelliferyl β-D-glucuronide, and the glucuronide conjugates of the R—OH groups depicted in FIG. 2. Assays for β-glucuronidase activity, also known as GUS activity are provided in U.S. Pat. No. 5,268,463.

A. Repressor Gene and Gene Product

As noted above, this invention provides gene sequence and gene product for a glucuronide repressor. Glucuronide repressor genes may be isolated by genetic, biochemical, or immunological methods. Some of the suitable nucleic acid molecules include either DNA, RNA, or hybrid molecules that encode a protein comprising the amino acid sequence depicted in SEQ ID No. 2 or variants thereof, that hybridize under stringent conditions (e.g., 5× SSPE, 0.5% SDS, 1× Denhardt's at 65° C. or equivalent conditions; see, Ausubel supra, Sambrook, supra) to the complement of the nucleotide sequence depicted in SEQ ID No. 1, that are codon optimized for a particular host species and which encode a glucuronide repressor as discussed herein or variants thereof, and molecules that hybridize under stringent conditions to the complement of the codon optimized molecule.

As exemplified herein, a gene encoding a E. coli glucuronide repressor was identified genetically and by DNA sequence analysis. Other glucuronide repressors may be identified in genomic or cDNA libraries by cross-hybridization with the E. coli repressor gene sequence, by complementation, by function, or by antibody screening on an expression library (see Sambrook et al., infra Ausubel et al, infra for methods and conditions appropriate for isolation of a glucuronide repressor from other species). Merely as an example, the isolation of the E. coli glucuronide repressor is provided herein.

Glucuronide repressor genes and proteins

The existence of a glucuronide repressor in E. coli (gusR) was established by genetic and biochemical experiments and genetically mapped to a region upstream of the glucuronidase gene (gusA). Moreover, gusR repression of β-glucuronidase activity has been shown by Northern analysis to down-regulate transcription of gusA. RNA from uninduced cultures of E. coli showed no hybridization to a gusA probe, in contrast to the strong hybridization observed to RNA extracted from cultures that had been induced by methyl β-D-glucuronide (Jefferson, supra). GusR acts by binding to gusA operator sequences, thus preventing transcription, this repression being relieved when a glucuronide substrate binds to the repressor and inactivates it.

A chromosomal region of E. coli known to encode gusA (encoding beta-glucuronidase, U.S. Pat. No. 5,268,463) and gusB (encoding the glucuronide permease, U.S. Pat. No. 5,432,081) was cloned as a Pst I-Hind III fragment from digested E. coli genomic DNA into a low-copy plasmid vector pRK404 (pKW212) or a high copy vector, pBSIISK+ (pKW214). It had previously been shown that cloning a smaller fragment containing the gusA and gusB genes alone gave rise to high levels of constitutive GUS activity as measured in cell extracts using the substrate p-nitrophenyl-glucuronide. However, clones pKW212 and pKW214, extending several kilobases in either direction of gusA and gusB, did not give constitutive activity, but required induction by addition of a GUS substrate, such as p-nitrophenyl-glucuronide. Thus, the larger Pst I-Hind III DNA fragment contained a gene capable of repressing the transcription of gusA and gusB, and the repression could be relieved by the addition of a substrate molecule.

Figure 3:
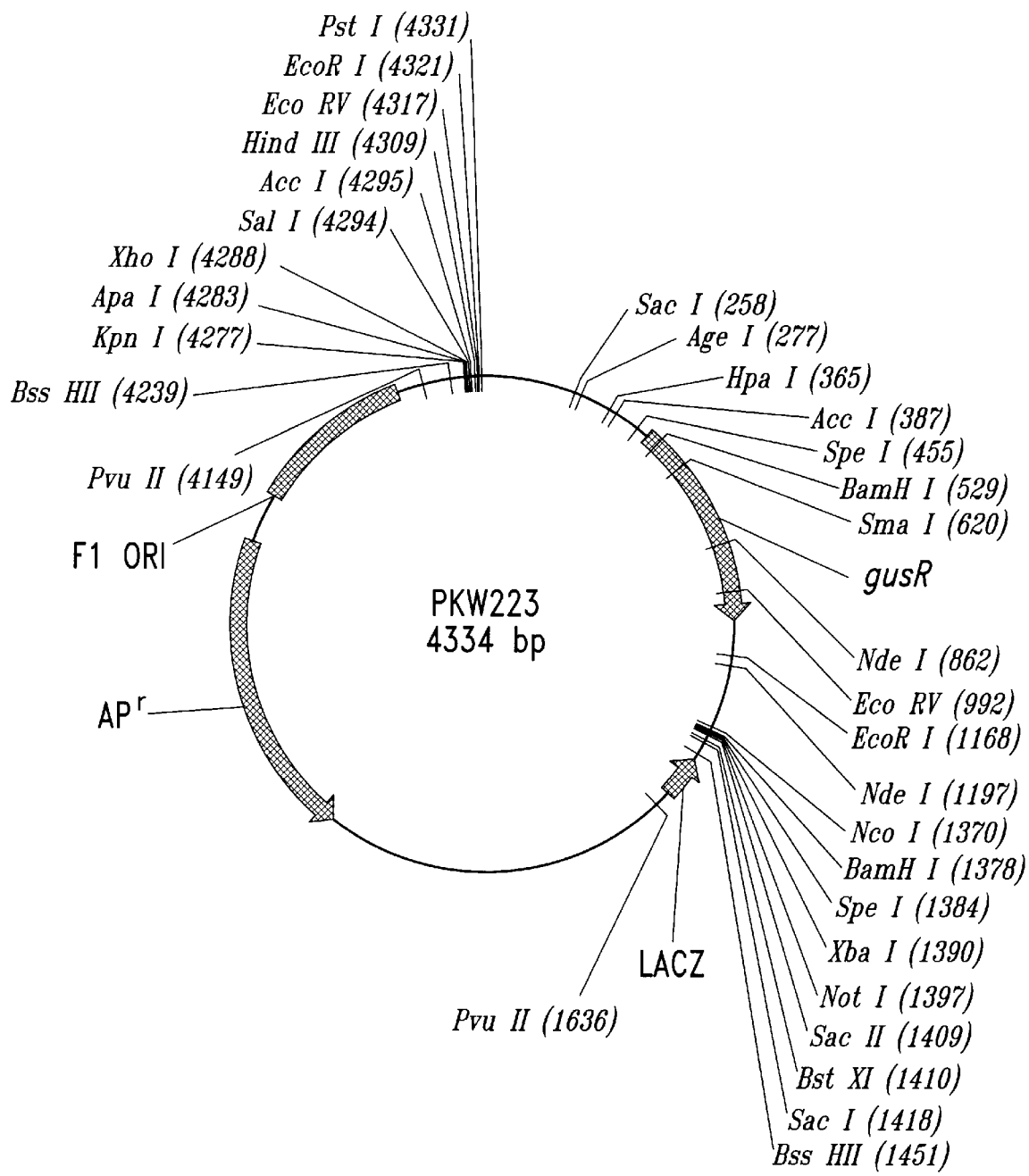
FIG. 3 is a map of pKW223. This plasmid contains a 1.4 kb BstXI-NcoI fragment harboring the gusR gene.

Two subclones of the Pst I-Hind III fragment of pKW212 were generated, the first being a large EcoR I-Hind III fragment known to comprise the gus promoter and the gusABC genes (pKW222). The second subclone was constructed from an approximately 1.4 kb BstX I-Nco I fragment, which extended from a BstX I site 3' of the Pst I site to an Nco I site downstream of the unique EcoR I site. This fragment, which mapped upstream of gusA, was cloned to create pKW223 (FIG. 3).

pKW222, when transformed into a strain deleted for the entire gus operon region (KW1) shows a high level of constitutive GUS activity. However, when this transformed strain is further transformed with the compatible plasmid pKW223, virtually all the activity is eliminated, indicating that pKW223 comprises a gene or DNA sequence which can repress the expression of the gus operon. Moreover, this repression is reversible by addition of a suitable inducer molecule such as X-glcA (5-bromo-4-chloro-3-indolyl-β-D-glucuronide). This is demonstrated by the production of deep blue colonies when plated on the indigogenic substrate X-glcA.

The DNA sequence of the GUS gene region was determined from the inserts of pKW222 and pKW223 and is presented in SEQ. ID NO: 4. The gusABC genes were identified, and coding sequence for gusA begins at nucleotide 1466. Two large open reading frames 5' of gusA were identified at nucleotides 1–264 and 485– 1075. The 5'-most reading frame was identified as a partial coding sequence for 7-alpha-hydroxysteroid dehydrogenase. The predicted amino acid sequence of the second open reading frame has significant sequence similarity to other bacterial transcriptional repressors, thus providing evidence that this open reading frame encodes gusR. The predicted repressor protein is 195 amino acids; the translational start codon, which was determined by N-terminal amino acid sequence analysis on purified gusR protein, is the second methionine residue in the open reading frame (SEQ ID No: 2; nucleotide 488 in SEQ ID No.:4). The repressor protein appears to have three domains: a DNA binding domain of approximately 60 amino acids; a glucuronide binding domain of from about 100 to 140 amino acids; and a domain of about 40 amino acids that has a leucine zipper similar to other transcription factors and which may mediate dimerization. The precise boundaries of these domains, and whether there are two or three separable domains, has not been definitively established, however the minimal sequence necessary for function of the domains is identifiable by the assays described herein.

In other aspects of this invention, isolated glucuronide repressor proteins or glucuronide-binding proteins are provided. In addition, depending upon the use of the repressor protein, it may be desirable that such proteins bind a variety of glucuronides or as few as one specific glucuronide. Specificity of binding is achieved by creating a variant of the glucuronide and testing the variant for the desired activity. Variants of the DNA binding domain to create higher or lower affinity and of the dimerization domain to increase or abolish dimerization potential are also useful within the context of this invention.

Variants of a glucuronide repressor include amino acid substitutions, deletions, insertions, and fusion proteins and are constructed by any of the well known methods in the art (see, generally, Ausubel et al., supra; Sambrook et al., supra). Such methods include site-directed oligonucleotide mutagenesis, restriction enzyme digestion and removal of bases or insertion of bases, amplification using primers containing mismatches or additional nucleotides, and the like. Variants of a DNA sequence of a glucuronide repressor include the nucleotide changes necessary to express a repressor protein having amino acid substitutions, deletions, insertions, and the like and nucleotide changes that result from alternative codon usage. For example, if the repressor protein is expressed in a heterologous species, codon optimization for that species may be desireable.

In addition to directed mutagenesis in which one or a few amino acids are altered, variants that have multiple substitutions may be generated. The substitutions may be scattered throughout the protein or functional domain or concentrated in a small region. For example, the operator-binding domain is mutagenized in the region of likely DNA contact residues by oligonucleotide-directed mutagenesis in which the oligonucleotide contains a string of dN bases or the region is excised and replaced by a string of dN bases. Thus, a population of variants with a randomized amino acid sequence in a region is generated. The variant with the desired properties (e.g., higher binding affinity to the glucuronide operator) is then selected from the population. In similar manner, multiple variants of the glucuronide-binding domain are generated. These variants are selected for binding to a particular glucuronide, preferably to the exclusion of or with much lower affinity to other glucuronides.

In other embodiments, the repressor protein comprises a fusion protein of a glucuronide-binding domain and a sequence-specific DNA binding domain or a fusion protein of a repressor and a molecule that binds the aglycon portion of the glucuronide. Construction of these fusion proteins is preferably accomplished by amplification of the desired domain regions and ligation of the amplified products. One of skill in the art recognizes that other routine methods and procedures may be alternatively used.

The glucuronide repressors will have at least a DNA binding domain and a glucuronide binding domain. For most repressors molecules, these domains are distinct sequences, although overlap of sequence is possible. For example, the dimerization domain of a repressor protein may be inseparable from another functional domain. In E. coli, the gusR repressor has a DNA binding domain comprising approximately the first 60 to 65 residues, and the glucuronide binding domain comprising approximately residues 60–65 to 160. These domains may be somewhat larger or smaller and assays for determining the boundaries of these domains are provided herein. For construction of the repressor, oligonucleotide primer sequences are derived from residues flanking the glucuronide binding domain are synthesized and used to amplify the domain. Restriction sites are preferably included in the primers to facilitate ligation and cloning. Similarly, primers flanking a DNA binding domain, selected from a DNA-binding protein, such as for cro, lac repressor, glucocorticoid receptor, trp repressor, TFIIIA, Sp-1, GCN4, AP-2, GAL4 repressor and any transcription factor, including activators and repressors with a known DNA sequence that the factor binds, are useful within the context of this invention (see, Sauer and Pabo, Ann. Rev. Biochem. 61: 1053–1095, 1992). Compatible restriction sites are preferably incorporated into the primers, such that the products when joined are in the same reading frame. Amplified products of the two domains are restricted and ligated together and inserted into an appropriate vector. Verification of the resulting clone is readily done by restriction mapping and DNA sequence analysis. DNA sequence analysis is preferable so that an in-frame reading frame can be verified.

In similar manner, a fusion protein of a repressor and an amino acid sequence that binds the aglycon are constructed. The repressor may be the glucuronide repressor or a fusion protein as described above. The amino acid sequence that binds the aglycon includes, but is not limited to, single chain antibodies, natural substrates or ligands, and the like. The additional part of the fusion protein is designed to confer increased specificity of the repressor for the glucuronide.

Vectors, host cells and means of expressing and producing protein

The glucuronide repressor may be expressed in a variety of host organisms. Preferably, the repressor is produced in bacteria, such as *E. coli*, for which many expression vectors have been developed and are available. Other suitable host organisms include other bacterial species, and eukaryotes, such as yeast (e.g., *Saccharomyces cerevisiae*), mammalian cells (e.g., CHO and COS-7), and insect cells (e.g., Sf9).

A DNA sequence encoding the repressor is introduced into an expression vector appropriate for the host. The repressor sequence is derived from an existing cDNA or synthesized. A preferred means of synthesis is amplification of the gene from cDNA using a set of primers that flank the coding region or the desired portion of the protein. As discussed above, the repressor sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At minimum, the vector must contain a promoter sequence. Other regulatory sequences may be included. Such sequences include a transcription termination signal sequence, secretion signal sequence, origin of replication, selectable marker, and the like. The regulatory sequences are operationally associated with one another to allow transcription or translation.

The plasmids used herein for expression of glucuronide repressor include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, RSV LTR, SV40, metallothionein promoter (see, e.g., U.S. Pat. No. 4,870,009) and other inducible promoters. For expression of the proteins, a promoter is inserted in operative linkage with the coding region for the glucuronide repressor.

The promoter controlling transcription of the glucuronide repressor may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the *E. coli* lacI repressor responsive to IPTG induction, the temperature sensitive λcI857 repressor, and the like. The *E. coli* lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in bacterial cells. Thus, the vector preferably contains a bacterial origin of replication. Preferred bacterial origins of replication include the f1-ori and col E1 origins of replication, especially the ori derived from pUC plasmids.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk-hosts). However, drug markers are also available (e.g., G418 resistance and hygromycin resistance).

The sequence of nucleotides encoding the glucuronide repressor may also include a secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184: 99–105, 1985). Prokaryotic and eukaryotic secretion signals that are functional in *E. coli* (or other host) may be employed. The presently preferred secretion signals include, but are not limited to, those encoded by the following *E. coli* genes: pelB (Lei et al., *J Bacteriol.* 169: 4379, 1987), phoA, ompA, ompT, ompF, ompC, beta-lactamase, and alkaline phosphatase.

One skilled in the art appreciates that there are a wide variety of suitable vectors for expression in bacterial cells and which are readily obtainable. Vectors such as the pET series (Novagen, Madison, Wis.) and the tac and trc series (Pharmacia, Uppsala, Sweden) are suitable for expression of a glucuronide repressor. Baculovirus vectors, such as pBlueBac (see, e.g., U.S. Pat. Nos. 5,278,050, 5,244,805, 5,243,041, 5,242,687, 5,266,317, 4,745,051, and 5,169,784; available from Invitrogen, San Diego) may be used for expression of the repressor in insect cells, such as *Spodoptera frugiperda* sf9 cells (see, U.S. Pat. No. 4,745,051).

The choice of a bacterial host for the expression of a glucuronide repressor is dictated in part by the vector. Commercially available vectors are paired with suitable hosts.

Repressor protein is isolated by standard methods, such as affinity chromatography, size exclusion chromatography, ionic exchange chromatography, HPLC, and other known protein isolation methods. (see generally Ausubel et al. supra; Sambrook et al. supra). An isolated purified protein gives a single band on SDS-PAGE when stained with Coomassie blue.

Preferably, the repressor protein is expressed as a hexahis fusion protein and isolated by metal-containing chromatography, such as nickel-coupled beads. Briefly, a sequence encoding His$_6$ is linked to a DNA sequence encoding a repressor. Although the His$_6$ sequence can be positioned anywhere in the molecule, preferably it is linked at the 3' end immediately preceding the termination codon. The His-gusR fusion may be constructed by any of a variety of methods. A convenient method is amplification of the gusR gene using a downstream primer that contains the codons for His$_6$ (see Example 3C).

A repressor protein can also be purified by virtue of its binding to β-glucuronides that are competitive inhibitors of β-glucuronidase. The glucuronides are coupled to an affinity matrix, such as Separose or agarose, through a carbodiimide-medated crosslinking or other suitable method. For example, phenylthio-β-D-glucuronide-SEPHAROSE CL6B and saccharolactone-agarose (Biosynth AG, Switzerland) both bind gusR protein and can be eluted from the matrix with an appropriate salt concentration.

Assays for function of glucuronide repressor protein

Repressor activity is conveniently measured by a variety of assays, including genetic and biochemical assays. Briefly, a strain deleted for the entire gus operon (e.g., KW1) is transformed by a plasmid containing the operator region and gusABC genes. Alternatively, a strain deleted for the repressor gene sequences may be used. Such a strain constitutively expresses gusA, the activity of which may be readily detected by a β-glucuronidase substrate, preferably a chromogenic substrate (e.g., 5-bromo-4-chloro-3-indoxyl-glucuronide) or fluorogenic substrate (e.g., 4-methlumbelliferone-glucuronide). This strain is further transformed with a plasmid that expresses the repressor or candidate repressor protein. If repressor activity is present, virtually all glucuronidase activity is eliminated. Repression is relieved by addition of a suitable glucuronide inducer. Variations of this assay, such as the choice of substrate, inducer, strain and vector constructs, may be made based on the teachings herein and in the art. Other in vitro assays, such as DNA footprinting in the presence and absence of a β-glucuronide inducer, may also be used to assay repressor activity.

Additional in vitro assays and methods for measuring the binding of the repressor to DNA and for measuring the binding of a glucuronide to the repressor involve biosensors or chip-based technologies. With biosensors, such as the BIA core (Pharmacia Biosensor AB, Uppsala, Sweden) or the apparatus disclosed in U.S. Pat. No. 5,395,587, functional characterization of protein-ligand and protein-DNA interactions are measured in real time using surface plasmon resonance detectors. (See, generally, Malmqvist, *Nature* 361: 186, 1993; Coulet and Bardeletti, *Biochem. Soc. Trans.* 19: 1, 1991; Robinson, *Biochem. Soc. Trans.* 19: 18–20, 1991; and Downs, *Biochem. Soc. Trans.* 19: 39–43, 1991). Chip-based technology such as described in U.S. Pat. No. 5,412,087; WO 95/22058, U.S. application Ser. No. 08/28, 454 now abandoned, and WO 88/08875, may also be exploited for measuring binding.

As described herein, this invention provides repressor proteins that comprise the DNA-binding activity of a glucuronide repressor protein. The DNA-binding activity is the specific binding to a glucuronide operator sequence. Although a variety of in vivo and in vitro assays may be used to assess DNA binding, a genetic assay or a biosensor-based assay may be used. Briefly, in a genetic assay, the nucleotide sequence encoding a candidate binding protein is cloned into an expression vector. A strain is isolated or constructed that lacks the gusR gene or activity and contains a glucuronide operator sequence linked to a reporter gene, such that there is constitutive expression of the reporter gene. Preferably, a construct, such as pKW222 containing the operator and gusABC genes, is used, but other suitable and readily assayable reporter genes (e.g., β-galactosidase, luciferase) may be substituted for gusA. If the candidate binding protein binds to the operator, transcription and therefore enzymatic activity of gusA will be greatly diminished or eliminated. Alternatively, a mobility shift assay may be performed. Briefly, fragments of DNA containing a glucuronide operator sequence are obtained. Any suitable method for isolating these fragments may be used. For example, DNA fragments may be isolated after restriction digestion of a plasmid or other DNA that contains the operator sequence or by amplification of the operator region and purification of the amplified product. The fragments are radiolabeled and mixed with protein (see, Ausubel et al., supra, Chapter 12 for protocols). Reactions are electrophoresed through agarose or polyacrylamide gels and exposed to X-ray film. Specific protein-DNA interactions result in retarded mobility of the DNA fragment. Although less preferable, other methods may be used for detecting sequence-specific binding of proteins to DNA, including nitrocellulose filter binding, DNase I footprinting, methylation protection, and methylation interference.

In other aspects of this invention, proteins are provided that have the β-glucuronide binding activity of the glucuronide repressor. Such activity may be assayed in vitro or in vivo. For example, an in vitro assay may be performed by spotting the protein on nitrocellulose or electrophoresing protein and transferring protein to nitrocellulose and incubating radiolabeled, fluorescent or chromogenic glucuronide to the nitrocellulose. Any means of contacting the protein and β-glucuronide may be used. Furthermore, many β-glucuronide substrates are available that give a fluorescent or chromogenic signal upon binding or with subsequent cleavage by the addition of GUS. Bound glucuronide is then detected by autoradiography. Other in vitro assays include the biosensor-based assays described above. A suitable in vivo assay is performed by constructing a strain as described above, which contains the glucuronide operator and gus-ABC genes. Alternatively, another operator and reporter gene construct can be used as long as the cell can import the glucuronide. A vector construct capable of expressing a repressor protein having an operator-binding amino acid sequence fused to the candidate glucuronide-binding amino acid sequence. The test cell transfected with this construct will be repressed for expression of the reporter gene. A glucuronide is provided to the cell and causes derepression of the reporter gene if the repressor binds the glucuronide. By supplying different glucuronides in these assays, a pattern of discrimination for glucuronide binding is determined.

B. Uses of the Repressor to Control Gene Expression in Cells

Figure 4:
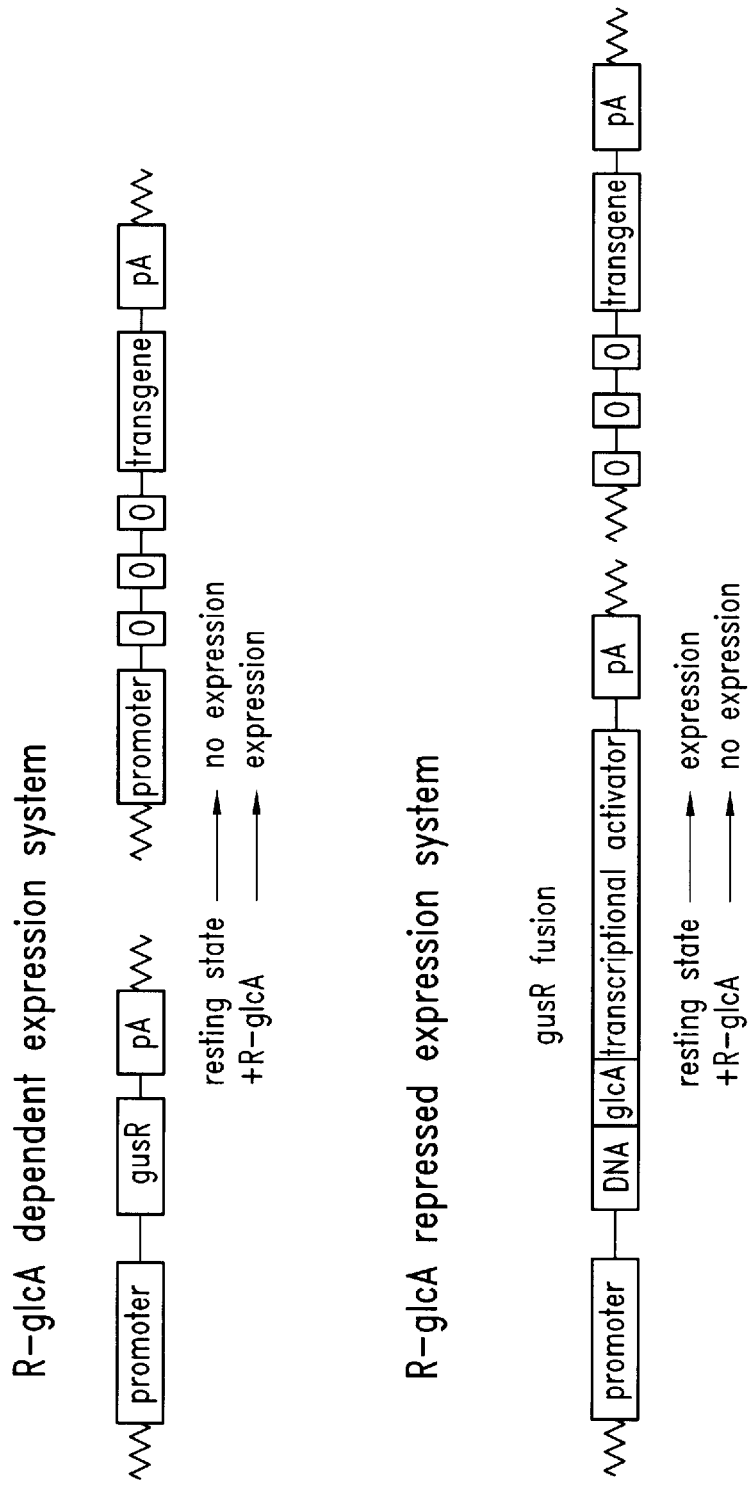
FIG. 4 is a schematic depicting two glucuronide repressor expression systems. The upper figure shows constructs used in a glucuronide (R-glcA) dependent expression system. The lower figure shows constructs used in a glucuronide repressed expression system. O, operator sequence; pA, polyadenylation signal; gusR fusion, a fusion protein comprising a DNA binding domain, a glucuronide binding domain and a transcriptional activation domain.

As discussed above, this invention provides vectors for the expression of transgenes under control of a glucuronide repressor. Within the context of this invention, a transgene is any gene sequence introduced into plant or animal cells. Two types of glucuronide repressor controlled systems are provided herein. One is a glucuronide-dependent expression system; the other is a glucuronide repressed expression system (FIG. 4).

In the glucuronide-dependent system, a vector is constructed containing two expression units. One unit comprises a glucuronide repressor, preferably gusR, under control of a promoter capable of expression in the host cell. The second unit comprises the transgene under control of a promoter, but glucuronide operator sites are located in between. In a resting state (without glucuronide inducer), the repressor is expressed, binds to the operator site(s) and interferes with transcription of the transgene. In the induced state, the glucuronide inducer binds to the repressor and causes release of the repressor from the operator site, thus allowing expression of the transgene (FIG. 4).

In the glucuronide-repressed expression system, two expression units are again provided. One unit comprises a fusion glucuronide repressor that has a glucuronide operator binding domain, glucuronide binding domain, and a transcriptional activator domain. The other unit comprises the transgene downstream of glucuronide operator sites. In the resting state, the fusion repressor binds to the operator and activates transcription. In the induced state, the fusion repressor binds to the glucuronide inducer and is released from the operator. Without a linked promoter, the transgene is not expressed (FIG. 4).

For each of these systems, one skilled in the art recognizes that additional elements, such as polyadenylation signals, splice sites, enhancers, and the like, may be necessary or optimal for expression of the repressor and transgene in the host cell. As well, the choice of a promoter for the repressor and for the transgene in the glucuronide-dependent system depends in part upon the host and tissue used for expression. For example, a tissue-specific promoter may be desirable to further control expression. Furthermore, the expression units may be provided in a single vector or in multiple vectors. As well, at least one operator sequence is provided, and preferably multiple operator sites in tandem array are used. Most preferably, from 1–10 operator sites are included.

Transcriptional activators are well known (see, Sauer and Pabo, supra). Certain activators, such as GAL4 and GCN4 have been successfully used in two-hybrid systems to activate gene expression and their activation domains are well characterized.

As described herein, in addition to β-glucuronides, β-glucuronide derivatives that are bound by a glucuronide repressor, but are not cleaved by β-glucuronidase, or that more readily pass a cell membrane are useful in these systems. Derivatives of glucuronides that are modified at the C6 position as an ester linkage, amide linkage, or the like, to be more hydrophobic provide a glucuronide that is more membrane permeant, but still binds to the repressor protein. Derivatives of glucuronides that are altered at the C1 position (e.g., through an —N—, —C—, or —S— linkage rather than an —O— linkage) are in general not susceptible to cleavage by β-glucuronidase. One exception is that an —N— linkage is cleavable by $E.$ $coli$ β-glucuronidase, but is not cleavable by human β-glucuronidase. As shown herein, phenyl-thio-β-D-glucuronide is bound by a glucuronidase repressor, but is not cleaved by β-glucuronidase. These types of derivatives are preferred in situation where the host cells express endogenous GUS activity. More preferred β-glucuronide derivatives are doubly modified to be more membrane permeable (i.e., more hydrophobic) and bind glucuronidase repressor but not cleaved by endogenous β-glucuronidase. One example of this class of derivatives has a methyl ester at the C6 position and a thio ether linkage at C1 to the aglycone. Other hydrophobic groups (e.g., ethyl ester; propyl ester) and other ether linkages (e.g., —C—; —N—) may be interchanged. Suitable hydrophobic groups and ether linkages are well known.

Transgenes for expression

Preferred transgenes for introduction into plants encode proteins that affect fertility, including male sterility, female fecundity, and apomixes; plant protection genes, including proteins that confer resistance to diseases, bacteria, fungus, nemotodes, viruses and insects; genes and proteins that affect developmental processes or confer new phenotypes, such as genes that control development of meristem, timing of flowering, and the such.

Insect and disease resistance genes are well known. Some of these genes are present in the genome of plants and have been genetically identified. Others of these genes have been found in bacteria and are used to confer resistance.

Particularly well known insect resistance genes are the crystal genes of *Bacillus thuringiensis*. The crystal genes are active against various insects, such as lepidopterans, Diptera, and mosquitos. Many of these genes have been cloned. For examples, see, GenBank Accession Nos. X96682, X96684; M76442, M90843, M89794, M22472, M37207, D17518, L32019, M97880, L32020, M64478, M11250, M13201, D00117, M73319, X17123, X86902, X06711, X13535, X54939, X54159, X13233, X54160, X56144, X58534, X59797, X75019, X62821, Z46442, U07642, U35780, U43605, U43606, U10985; U.S. Pat. No. 5,317,096, U.S. Pat. No. 5 5,254,799; U.S. Pat. No. 5,460,963, U.S. Pat. No. 5,308,760, U.S. Pat. No. 5,466,597, U.S. Pat. No. 5,2187,091, U.S. Pat. No. 5,382,429, U.S. Pat. No. 5,164,180, U.S. Pat. No. 5,206,166, U.S. Pat. No. 5,407,825, U.S. Pat. No. 4,918,066; PCT Applications WO 95/30753, WO 94/24264; AU 9062083; EP 408403 B1, EP 142924 B1, EP 256,553 B1, EP 192,741 B1; JP 62-56932;. Gene sequences for these and related proteins may be obtained by standard and routine technologies, such as probe hybridization of a *B. thuringiensis* library or amplification (see generally, Sambrook et al., supra, Ausubel et al. supra). The probes and primers may be synthesized based on publicly available sequence information.

Other resistance genes to Sclerotinia, cyst nematodes, tobacco mosaic virus, flax and crown rust, rice blast, powdery mildew, verticillum wilt, potato beetle, aphids, as well as other infections, are useful within the context of this invention.

Examples of such disease resistance genes may be isolated from teachings in the following references: isolation of rust disease resistance gene from flax plants (WO 95/29238); isolation of the gene encoding Rps2 protein from *Arabidopsis thaliana* that confers disease resistance to pathogens carrying the avrRpt2 avirulence gene (WO 95/28478); isolation of a gene encoding a lectin-like protein of kidney bean confers insect resistance (JP 71-32092); isolation of the Hm1 disease resistance gene to *C. carbonum* from maize (WO 95/07989); for examples of other resistance genes, see WO 95/05743; U.S. Pat. No. 5,496,732; U.S. Pat. No. 5,349,126; EP 616035; EP 392225; WO 94/18335; JP 43-20631; EP 502719; WO 90/11770; U.S. Pat. No. 5,270,200; U.S. Pat. Nos. 5,218,104 and 5,306,863). In addition, general methods for identification and isolation of plant disease resistance genes are disclosed (WO 95/28423). Any of these gene sequences suitable for insertion in a vector according to the present invention may be obtained by standard recombinant technology techniques, such as probe hybridization or amplification. When amplification is performed, restriction sites suitable for cloning are preferably inserted.

Nucleotide sequences for other transgenes, such as controlling male fertility, are found in U.S. Pat. No. 5,478,369, references therein, and Mariani et al., *Nature* 347: 737, 1990.

Vectors, host cells, and methods for transformation

As noted above, the present invention provides vectors capable of expressing transgenes under the control of a glucuronide repressor. In agricultural applications, the vectors should be functional in plant cells. At times, it may be preferable to have vectors that are functional in *E. coli* (e.g., production of protein) or animal cells. Vectors and procedures for cloning and expression in *E. coli* and animal cells are discussed above and, for example, in Sambrook et al (supra) and in Ausubel et al. (supra).

Vectors that are functional in plants are preferably binary plasmids derived from Agrobacterium plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable marker and a reporter gene are also included. The vector also preferably contains a bacterial origin of replication.

As discussed above, this invention provides the expression of a transgene in plants or animals under control of a glucuronide repressor. The choice of the transgene depends in part upon the desired result. For example, when plant resistance is desired, a preferred gene is specific to the disease or insect.

In certain preferred embodiments, the vector contains a reporter gene. The reporter gene should allow ready determination of transformation and expression. The GUS (β-glucoronidase) gene is preferred (U.S. Pat. No. 5,268, 463). Other reporter genes, such as β-galactosidase, luciferase, GFP, and the like, are also suitable in the context of this invention. Methods and substrates for assaying expression of each of these genes are well known in the art. The reporter gene should be under control of a promoter that is functional in host cells, such as the CaMV 35S promoter in plants.

The vector should contain a promoter sequence for the glucuronide repressor gene and in certain embodiments for the transgene as well. Preferably, for expression of a transgene in plants, the promoter is the CaMV 35S promoter.

Preferably, the vector contains a selectable marker for identifying transformants. The selectable marker preferably confers a growth advantage under appropriate conditions. Generally, selectable markers are drug resistance genes, such as neomycin phosphotransferase. Other drug resistance genes are known to those in the art and may be readily substituted. The selectable marker also preferably has a linked constitutive or inducible promoter and a termination sequence, including a polyadenylation signal sequence.

Additionally, a bacterial origin of replication and a selectable marker for bacteria are preferably included in the vector. Of the various origins (e.g., colEI, fd phage), a colEI origin of replication is preferred. Most preferred is the origin from the pUC plasmids, which allow high copy number.

A general vector suitable for use in the present invention is based on pBI121 (U.S. Pat. No. 5,432,081) a derivative of pBIN19. Other vectors have been described (U.S. Pat. No. 4,536,475) or may be constructed based on the guidelines presented herein. The plasmid pBI121 contains a left and right border sequence for integration into a plant host chromosome. These border sequences flank two genes. One is a kanamycin resistance gene (neomycin phosphotransferase) driven by a nopaline synthase promoter and using a nopaline synthase polyadenylation site. The second is the E. coli GUS gene (reporter gene) under control of the CaMV 35S promoter and polyadenlyated using a nopaline synthase polyadenylation site. Either one of the expression units described above is additionally inserted or is inserted in place of the CaMV promoter and GUS gene. Plasmid pBI 121 also contains a bacterial origin of replication and selectable marker.

Vectors suitable for expression in animal cells are well known in the art and are generally described in Ausubel et al., supra and Sambrook et al., supra. In addition, transformation methods are well known and include electroporation, direct injection, $CaPO_4$-mediated transfection and the like.

Plant transformation methods

Plants may be transformed by any of several methods. For example, plasmid DNA may be introduced by Agrobacterium co-cultivation or bombardment. Other transformation methods include electroporation, $CaPO_4$-mediated transfection, and the like. Preferably, vector DNA is first transfected into Agrobacterium and subsequently introduced into plant cells. Most preferably, the infection is achieved by co-cultivation. In part, the choice of transformation methods depends upon the plant to be transformed. For example, monocots generally cannot be transformed by Agrobacterium. Thus, Agrobacterium transformation by co-cultivation is most appropriate for dicots and for mitotically active tissue. Non-mitotic dicot tissues can be efficiently infected by Agrobacterium when a projectile or bombardment method is utilized. Projectile methods are also generally used for transforming sunflowers and soybean. Bombardment is used when naked DNA, typically Agrobacterium or pUC-based plasmids, is used for transformation or transient expression.

Briefly, co-cultivation is performed by first transforming Agrobacterium by freeze-thawing (Holsters et al., *Mol. Gen. Genet.* 163: 181–187, 1978) or by other suitable methods (see, Ausubel, et al. supra; Sambrook et al., supra). A culture of Agrobacterium containing the plasmid is incubated with leaf disks, protoplasts or meristematic tissue to generate transformed plants (Bevan, *Nucl. Acids. Res.* 12: 8711, 1984).

Briefly, for microprojectile bombardment, seeds are surface sterilized in bleach solution and rinsed with distilled water. Seeds are then imbibed in distilled water, and the cotyledons are broken off to produce a clean fracture at the plane of the embryonic axis. Explants are then bisected longitudinally between the primordial leaves and placed cut surface up on medium with growth regulating hormones, minerals and vitamin additives. Explants are bombarded with 1.8 μm tungsten microprojectiles by a particle acceleration device. Freshly bombarded explants are placed in a suspension of transformed Agrobacterium transferred to medium with the cut surfaces down for 3 days with an 18 hr light cycle. Explants are transferred to medium lacking growth regulators but containing drug for selection and grown for 2–5 weeks. After 1–2 weeks more without drug selection, leaf samples from green, drug-resistant shoots are grafted to in vitro grown rootstock and transferred to soil.

Glucuronide inducer is applied to the plants when a change in the state of expression of the transgene is desired. Any glucuronide that is transported into a cell is useful in the context of this invention. The vasculuture system of the plant distributes the inducer. The inducer enters cells either by passive diffusion or by the expression of a permease, which is also a transgene. Preferably, the glucuronide is not degraded by the host cell. Also, preferably, glucuronide is soluble in aqueous solutions. The glucuronide may be applied by spraying the plant, soil, provided in fertilizer, and the like.

C. Use of the Repressor in Diagnostics

As simple glycosides, β-glucuronides are extremely important as the most prominent of the two principal forms in which xenobiotics (compounds that are foreign to the body) and endogenous phenols and aliphatic alcohols are rendered biologically inert (detoxified) and excreted in the urine and bile of vertebrates (reviewed by Dutton, 1966, 1981).

The principal problem underlying detoxification in vertebrates, is that many compounds within the body, including endogenous biologically active molecules such as steroid hormones, bio-degradation products such as bilirubin, and foreign compounds (xenobiotics) that may have been introduced into the body in food or medicine, are lipophilic or fat soluble. Hence, they do not dissolve readily in urine or bile, the two major routes to removal of waste products from the body. This problem is overcome by conjugation of the lipophilic compounds to highly polar residues, such as glucuronic acid or a sulfate residue, making the resulting conjugate highly water soluble, and thus able to be excreted from the body.

Figure 5:
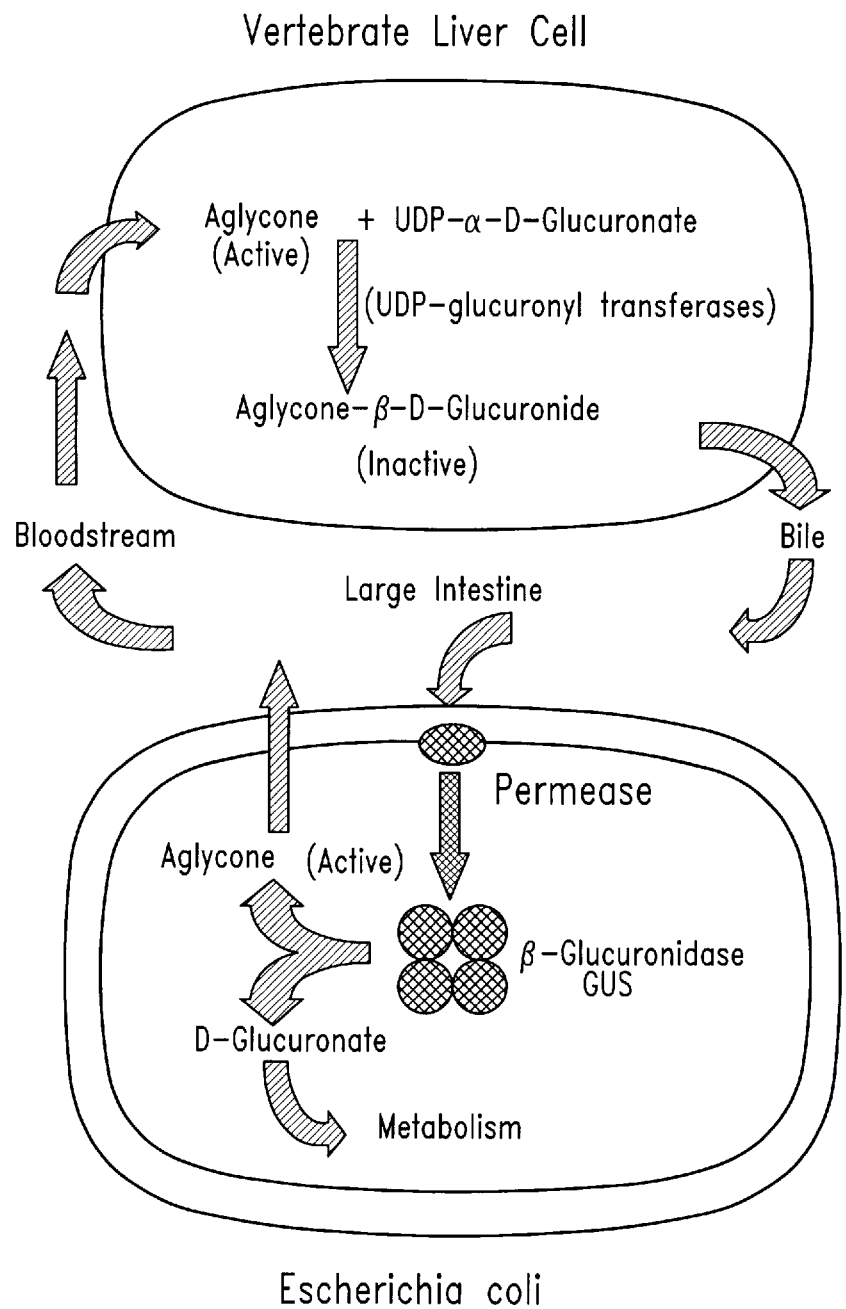
FIG. 5 depicts the enterohepatic circulation of glucuronide conjugates.

Glucuronidation occurs in many tissues in vertebrates, particularly in the liver. The reaction is carried out by a set of membrane-bound enzymes that catalyze the transfer of a glucuronate residue from uridine diphosphate 1-α-D- glucuronate to the aglycon (the aglycon is the residue being detoxified, to which the sugar molecule or glycon is bound). Several isozymes of UDP-glucuronyl transferase have been characterized, and these are reviewed in detail in Dutton (1980). These enzymes frequently form part of a collection of detoxifying enzymes, including hydroxylases and mixed-function oxidases, that work together to metabolize lipophilic, relatively insoluble compounds into the highly water-soluble glucuronide conjugates (as well as into sulfates and other derivatives). These conjugates are then excreted into the bile (for the larger glucuronide conjugates) or the urine. (See FIG. 5.)

Several thousand β-glucuronides have been identified in urine and bile as detoxication products. This includes many that form following oral administration of the free aglycon or a related compound, for example, as a drug during medical treatment, and an extensive list of known glucuronides can be found in Dutton (*Glucuronic Acid, Free and Combined,* Academic Press, New York 1966). In addition, many endogenous steroid hormones and bioactive substances, or bio-degradation products such as bilirubin, are conjugated and excreted as β-glucuronide conjugates. This process of conjugation with glucuronides is reversed by activity of the enzyme β-glucuronidase (GUS).

The ability of GUS to cleave a β-glucuronide conjugate depends upon two key steps: (1) the substrate must be taken up into the cell, generally mediated via the glucuronide permease, and (2) the substrate must be able to alleviate repression by the gus repressor.

The ability of a number of different glucuronides to induce GUS activity varies (e.g., methyl β-D-glucuronide at 1 mM concentration inducing a level of GUS activity approximately 15 times that of phenyl β-D-thioglucuronide). In addition, 5-bromo-4-chloro-3-indolyl β-D-glucuronide (X-Gluc), p-nitrophenyl β-D-glucuronide (PNPG), 4-methylumbelliferyl β-D-glucuronide (MUG) and resorufin glucuronide all act as powerful inducers. In general, values of GUS activity measured after 90' induction, starting with 1 mM external concentrations of these glucuronides, are of the order of 1–50 nmols PNPG hydrolyzed per minute per $OD_{600}$ unit of bacterial culture. Glucuronides that occur naturally in the body, including oestrogen glucuronide and testosterone glucuronide also have inducing ability (see Example 4 below).

The ability of the glucuronides to induce GUS, and therefore bind the repressor, may be used to assay the presence of glucuronides in a sample. Typically, for mammals and humans, in particular, the sample is preferably urine, but may also be bile obtained from the bile duct or large intestine, or sera. An assay for detecting glucuronides is as follows. Briefly, an operator sequence is bound with a glucuronide repressor. The sample is added, and if a glucuronide that binds to the repressor is present, the repressor is released from the operator. The unbound repressor is then detected. A glucuronide is present in a sample if the release of the repressor is higher than the release detected when a sample that does not contain the glucuronide is used.

The DNA sequence may be a glucuronide operator, but may alternatively be any sequence that the repressor specifically binds. For example, if the repressor is a fusion of a lac repressor DNA binding sequence and a glucuronide binding domain, the DNA sequence is the lac operator. Furthermore, the repressor may bind only a single glucuronide. Methods for generating and assaying such repressors are described herein.

Although this assay can be performed in solution, preferably the operator is bound to a solid substrate. Such solid substrates include beads, chips, biosensors and the like. Specific detection includes any means that distinguishes unbound repressor from bound repressor. Such means include colorometric, surface plasmon resonance, chemiluminescence, autoradiography and others known in the art.

D. Use of the Repressor to Purify Glucuronides

This invention provides methods to purify glucuronides using the binding characteristics of a glucuronide repressor. Briefly, a glucuronide repressor or glucuronide binding domain is attached, conjugated, or bound to a substrate. Alternatively, the repressor or domain is in solution. A sample containing a glucuronide is added for sufficient time to bind to the repressor. Preferably, the sample is added for a time to achieve equilibrium binding. Unbound material is washed away, and bound glucuronide is eluted. In general, elution occurs under non-physiological conditions, such as temperature shift, increased or decreased salt concentration, increased or decreased pH. (See, for example, Dean et al. *Affinity chromatography: a practical approach* IRL Press, Oxford, England, 1985.)

The repressor may be bound to a variety of matrices. Proteins are readily attached to agarose beads, dextran beads, nitrocellulose, polyacrylamide beads, magnetic beads, and the like. Methods for coupling to these and similar solid substrates are well known and a general discussion is found in Dean et al. (supra). In preferred embodiments, the repressor is isolated as a hexahis fusion protein, which is readily bound to a nickel column. Other fusion protein tags, such as S tag, T7 tag, HSV tag, are readily available (Novagen, Madison, Wis.), as well as kits containing the materials for binding the fusion protein. The repressor may alternatively be conjugated with biotin and bound to an avidin or streptavidin-conjugated substrate (e.g., streptavidin-agarose beads) either before or after contact with the sample.

When isolation of a specific glucuronide is desired, the glucuronide repressor used for isolation preferably binds that glucuronide specifically and either does not bind other glucuronides or binds others with a much lower affinity. A specific binding glucuronide repressor is either naturally found or is a variant generated by the methods described herein.

E. Use of the Repressor to Identify a Glucuronide Transport Protein from a Vertebrate This invention also provides methods for identifying a glucuronide transport protein from a vertebrate. As discussed above, GUS activity is found in essentially all vertebrates, implying that a specific transport protein is present. However, identification and isolation of such a protein has remained elusive. Clones expressing a glucuronide repressor are used to facilitate identification of a clone expressing a vertebrate transport protein.

Briefly, a cell that does not have GUS activity is transformed with a vector expressing gusR and a reporter or selectable gene linked to glucuronide operator sequences. In a resting state, the reporter gene is not expressed. When a glucuronide is added, there should be no expression of the reporter gene, indicating that the cell lacks a glucuronide transport protein. Suitable host cells include yeast and plants, and most bacteria. Transformed cells are then transfected with an expression library from a vertebrate, such as a human expression library. Such libraries are commercially available or are constructed by standard methodologies. Doubly transformed cells are treated with β-glucuronides and the appearance of the reporter or selectable gene is assayed. A selectable gene is preferred and examples of such genes include drug resistance genes (e.g., G418 resistance). Cells that transport the glucuronide express the reporter gene, and the clone responsible for transport is isolated and characterized.

The following examples are offered by way of illustration, and not by way of limitation.

EXAMPLES

Example 1

Cloning of the E. coli Glucuronide Repressor (gusR)

A chromosomal region of E. coli known to encode gusA, which encodes β-glucuronidase, (see, U.S. Pat. No. 5,268,463) and gusB, which encodes glucuronide permease (see, U.S. Pat. Nos. 5,268,463 and 5,432,081) is cloned as a Pst I-Hind III fragment from digested E. coli genomic DNA. The fragment is inserted into either a low-copy plasmid vector pRK404 (pKW212) or a high copy plasmid vector, pBSII SK+ (pKW214). When a clone containing only the gusA and gusB genes are transfected into a host cell, high levels of constitutive GUS activity are measured in extracts using the substrate p-nitrophenyl-glucuronide. In contrast, a host cell transfected with either clone containing the Pst I-Hind III fragment, which extends several kilobases in the 5' and 3' direction of gusA and gusB, did not have glucuronidase activity. However, glucuronidase activity is induced by addition of a GUS substrate, such as p-nitrophenyl-glucuronide. Thus, the Pst I-Hind III fragment contains a gene capable of repressing the transcription of gusA and gusB, and the repression is relieved by the addition of a substrate glucuronide molecule.

Identification of the repressor gene was facilitated by the construction of two subclones of the Pst I-Hind III fragment of pKW212. One subclone contained an EcoR I-Hind III fragment known to comprise the gus promoter and the gusABC genes (pKW222). A second subclone contained an approximately 1.4 kb BstX I-Nco I fragment (nucleotides 1 to 1368 of SEQ ID NO: 4), which maps downstream of the Pst I site and upstream of gusA. The fragment was cloned as a blunt-ended fragment into pBSIISK+ to create pKW223 (FIG. 3). The repressor is shown to reside on the 1.4 kb BstX I-Nco I fragment by the following transformation experiment. Strain KW1, which is deleted for the entire gus operon region, is transformed with pKW222. This transformant shows a high level of constitutive GUS activity. When this transformed strain is further transformed with the compatible plasmid pKW223, virtually all GUS activity is eliminated, indicating that pKW223 comprises a gene or DNA sequence that represses the expression of the gus operon. This repression is reversible by addition of the inducer molecule X-glcA (5-bromo-4-chloro-3-indolyl-β-D-glucuronide). This is demonstrated by the production of deep blue colonies when the doubly transformed cells are plated on the indigogenic substrate X-glcA.

The DNA sequence of the GUS gene region was determined from the inserts of pKW222 and pKW223 and is presented in SEQ. ID NO: 1. The gusABC genes were identified as beginning at nucleotide 1466. Two large open reading frames 5' of gusA were found from nucleotides 1–264 and 485–1075. The 5'most reading frame was identified as 7-alpha-hydroxysteroid dehydrogenase. The predicted amino acid sequence of the second open reading frame showed significant sequence similarity to other bacterial transcriptional repressors, thus providing evidence that this open reading frame codes for gusR. The predicted repressor protein is approximately 196 amino acids; the precise translational start codon is uncertain because there are three methionine residues at the N-terminal portion of the predicted protein (SEQ ID NO: 2). The repressor protein appears to have three domains: a DNA binding domain of approximately 60 amino acids; a glucuronide binding domain of from about 100 to 140 amino acids; and a domain of about 40 amino acids that has a leucine zipper similar to other transcription factors that may mediate dimerization. The precise boundaries of these domains, and whether there are two or three separable domains, is not definitively established.

Example 2

Identification of the E. coli Glucuronide Operator

Two approaches lead to identification of the operator sequence of the gus operon. In one approach, subclones of the operator region are constructed and tested for ability to titrate repressor away from operator sites on chromosomal DNA. In the second approach, particular sequences of interest within the operator region are synthesized, cloned into a high copy plasmid, and tested by repressor/operator titration experiments. (See FIGS. 8 and 9.)

Figure 6:
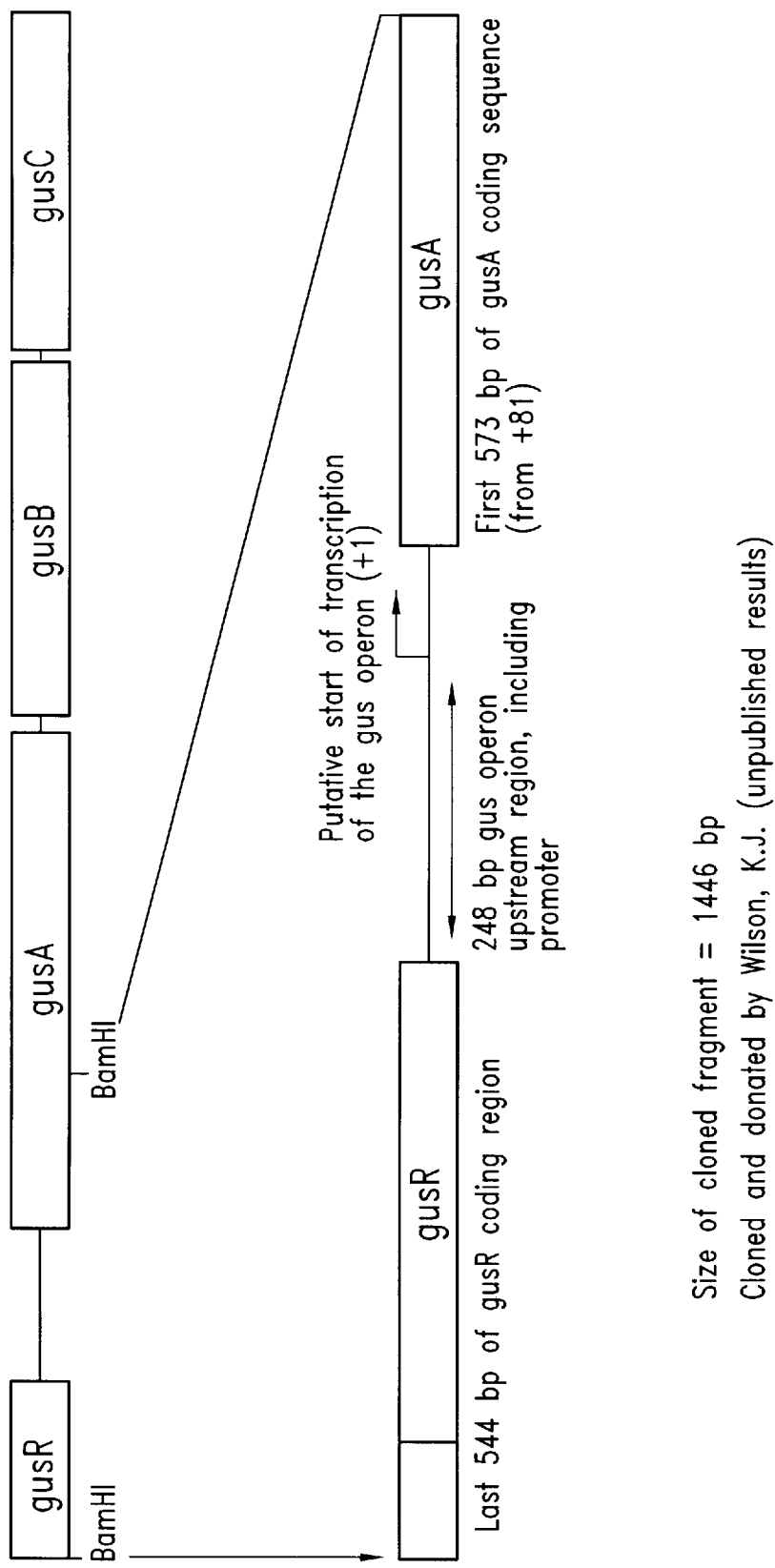
FIG. 6 is a map of the region of the gus operon claimed as a BamHI fragment.
Figure 7:
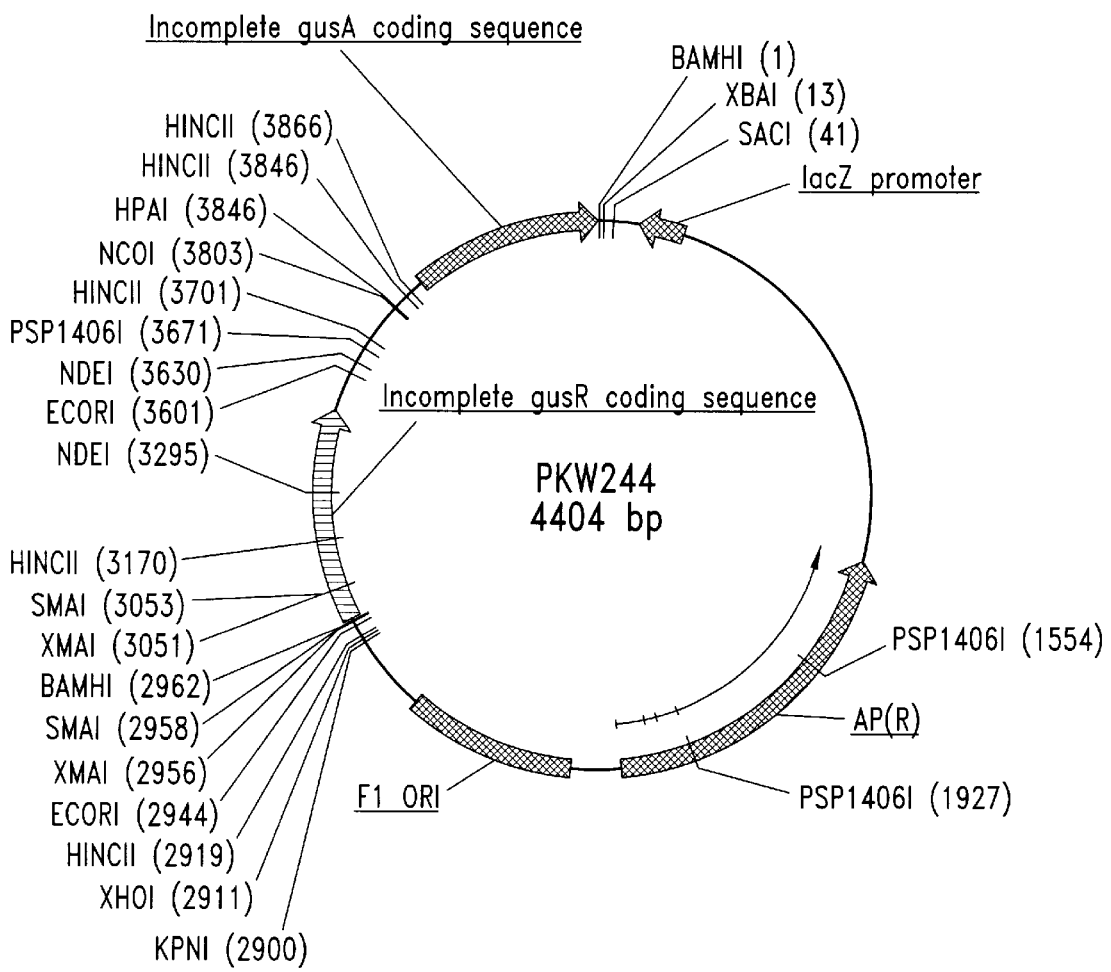
FIG. 7 is a restriction map of pKW244.

(1) A 1.4 kb BamHI-BamHI fragment containing the entire intergenic region between gusA (the first gene of the gus operon) and the upstream gene gusR was isolated and cloned into the vector pBSII(SK+) to create pKW244 (FIGS. 6 and 7). The BamHI fragment encompasses the main operator sites regulating the gus operon. Initial experiments confirmed that the insert of pKW244 does contain repressor binding sites. E. coli strain DH5α transformed with pKW244 yields blue colonies on plates containing X-gluc, indicating induction of the gus operon by repressor titration.

Subclones of the regulatory region were constructed (FIGS. 10–15). The β-glucuronidase activity of these clones is presented in the following Table and FIG. 15.

| Plasmid | Average amount of β-glucuronidase production (nmol pNP/min/mg protein) | 95% confidence limit | % of pKW244 β-glucuronidase production |
|---------|---|---|---|
| pKW244  | 943    | 154  | 100  |
| pBSIISK+| 1.26   | 0.6  | 0.1  |
| pMEL1   | 22.04  | 9.1  | 2.3  |
| pMEL3   | 926.5  | 486  | 98.2 |
| pMEL4   | 198.14 | 35.6 | 21   |
| pMEL5   | 254.9  | 31.2 | 27   |
| pMEL8   | 1.16   | 0.4  | 0.1  |

These results show that pMEL3, pMEL4, and pMEL5 contain operator sequences and thus, the operator region was narrowed.

Figure 8:
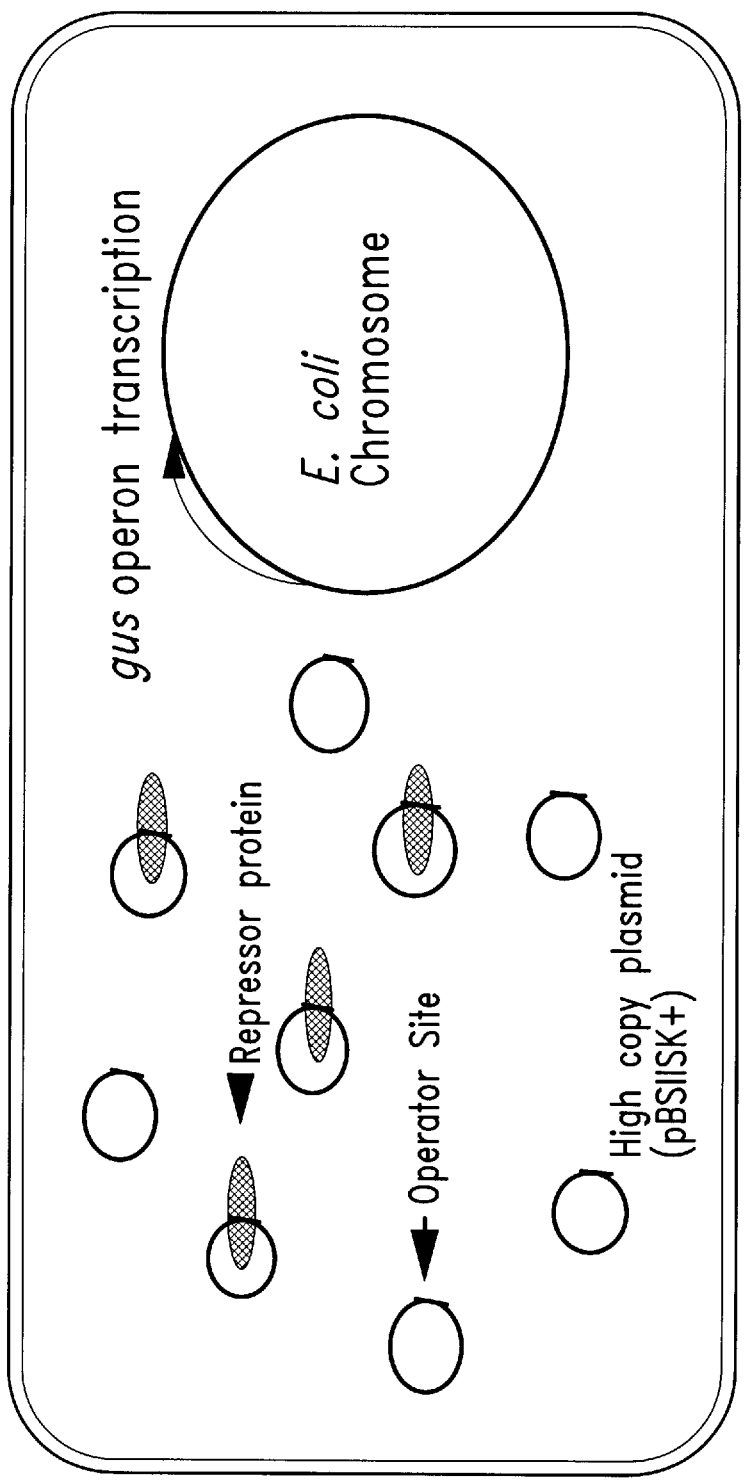
FIG. 8 depicts the strategy of an operator/repressor experiment. A high copy plasmid containing an operator site is introduced into a cell with a gus operon located on the *E. coli* chromosome. The operator binds available repressor allowing transcription of the gus operon.
Figures 9A, 9B:
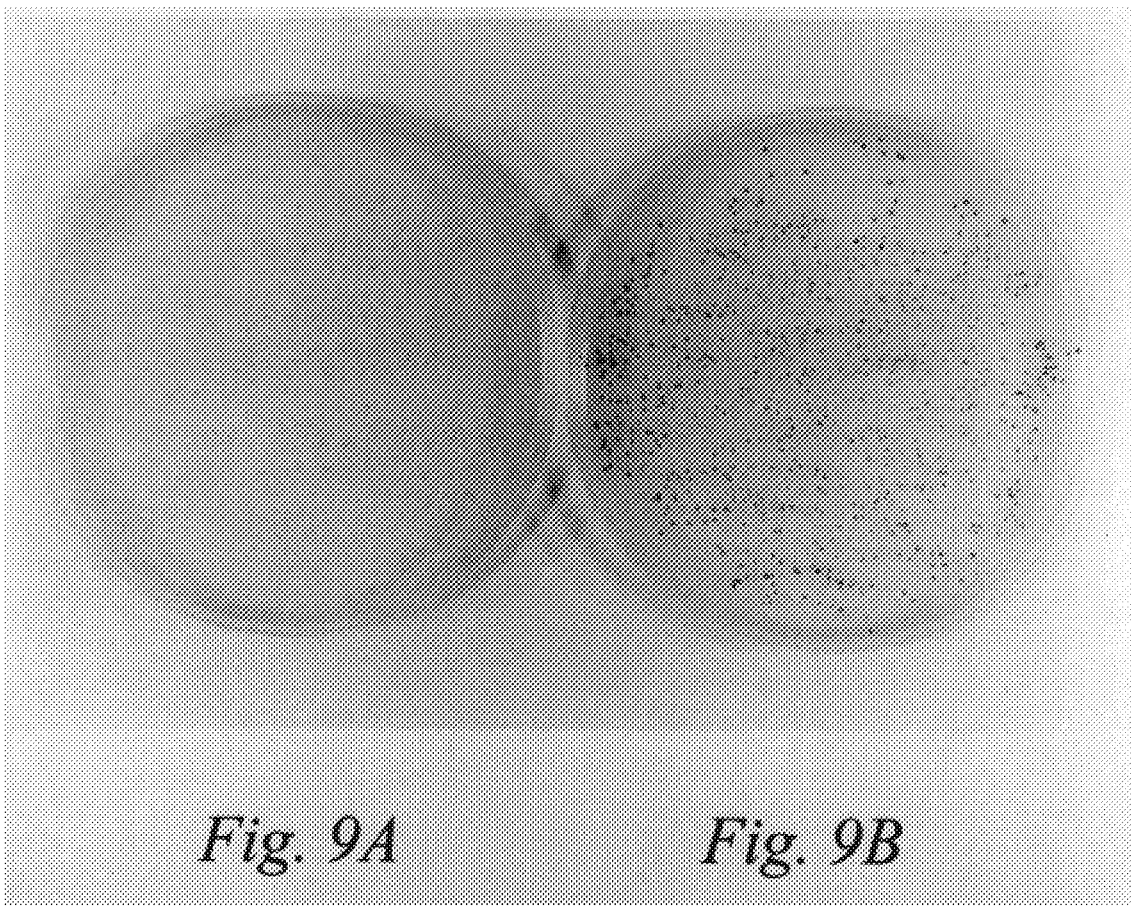
FIG. 9 shows an example of an operator/repressor titration experiment. A: DH5α cells transformed with pBSIISK+ and plated on LB media containing X-gluc. B: DH5α cells transformed with pKW244 and plated on LB media containing X-gluc. The gus operon is induced as shown by the presence of blue colonies.
Figure 10:
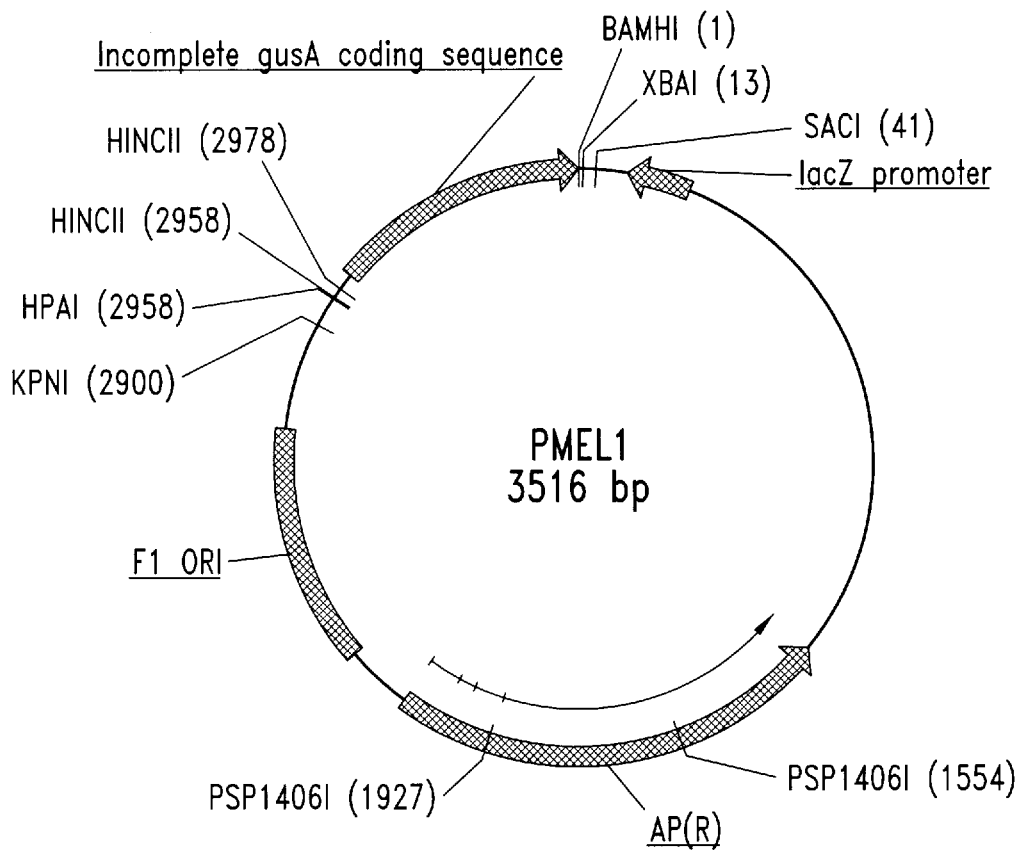
FIG. 10 is a restriction map of pMEL 1.
Figure 11:
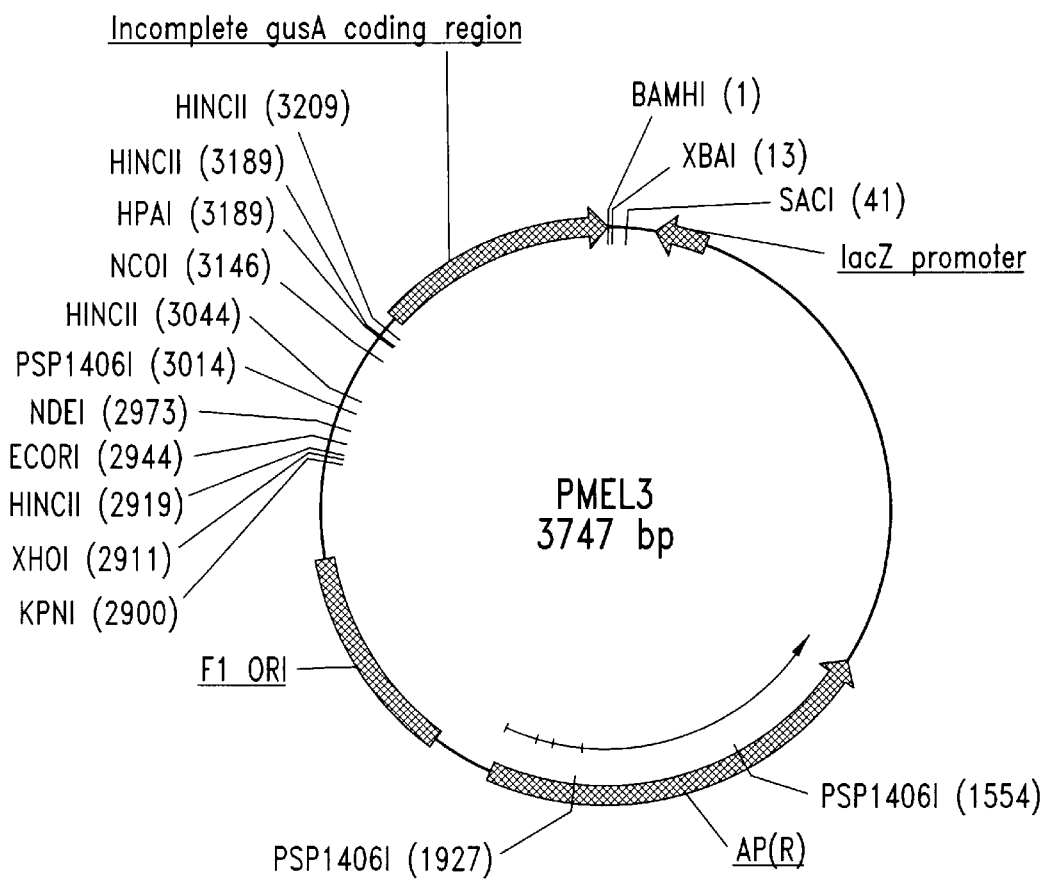
FIG. 11 is a restriction map of pMEL3.
Figure 12:
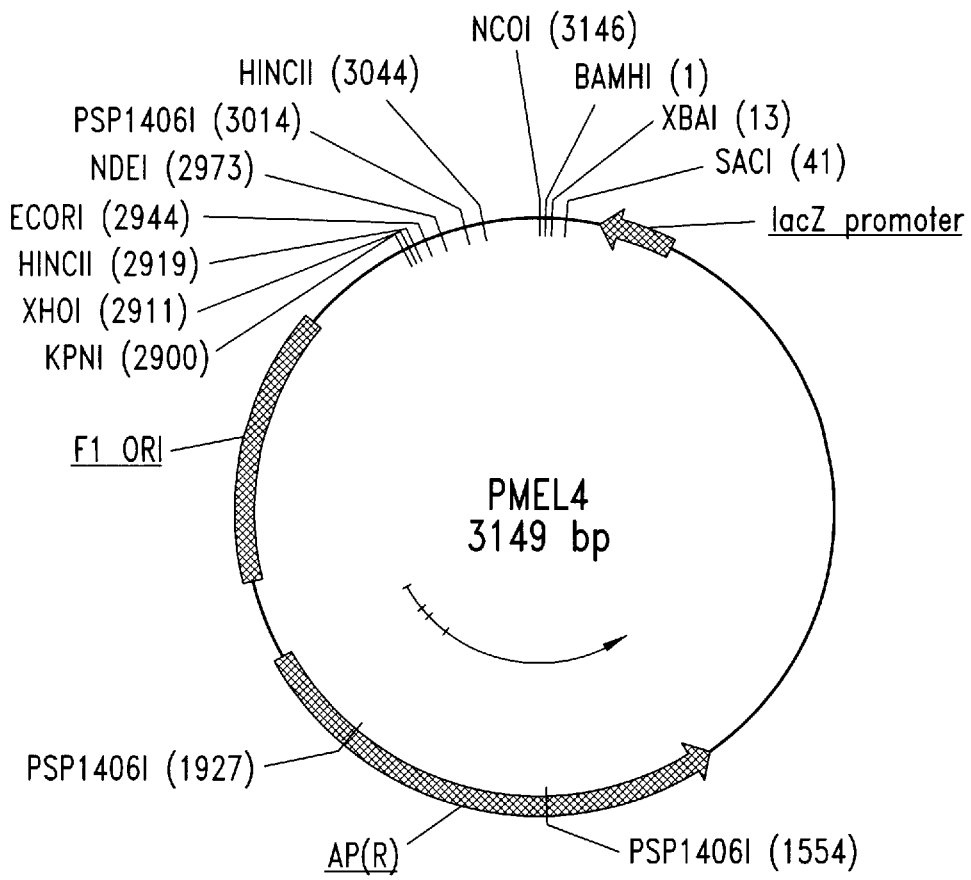
FIG. 12 is a restriction map of pMEL4.
Figure 13:
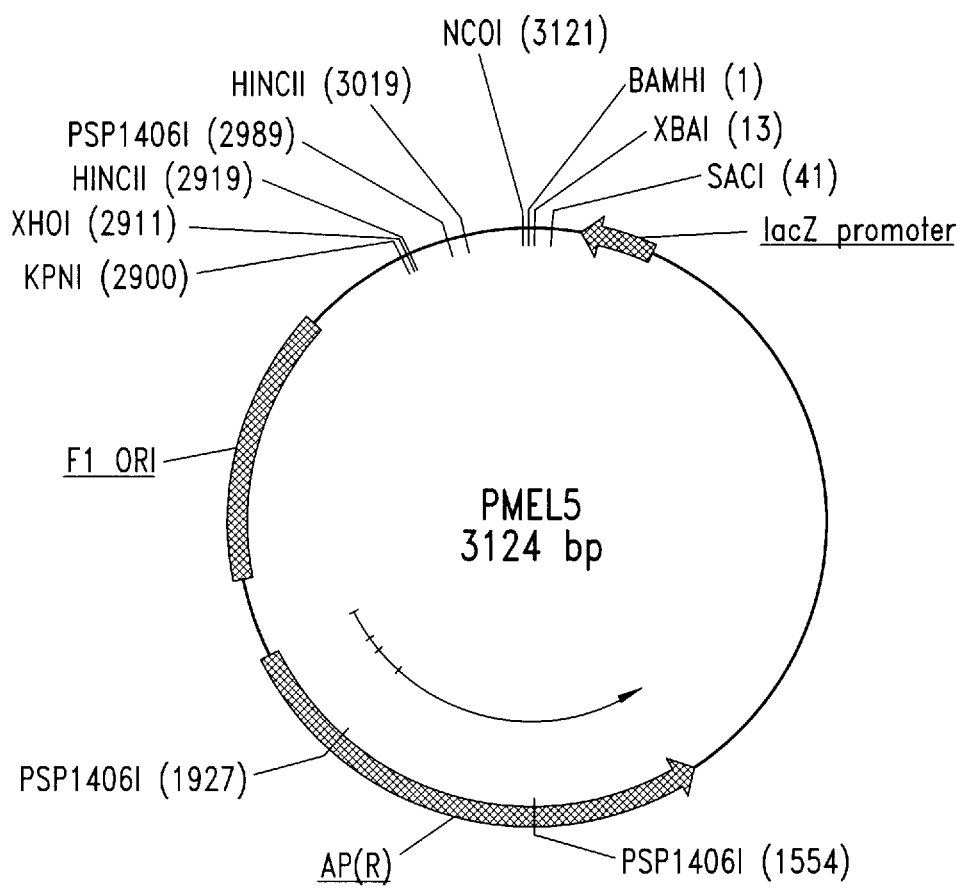
FIG. 13 is a restriction map of pMEL5.
Figure 14:
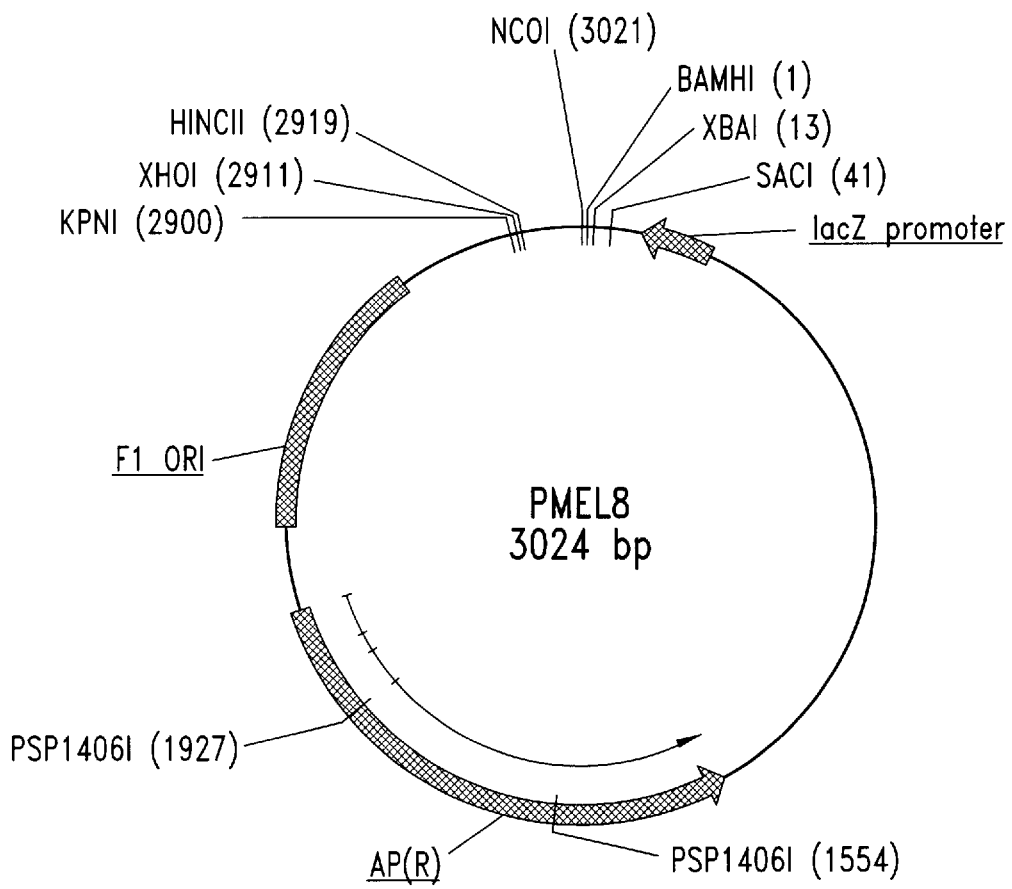
FIG. 14 is a restriction map of pMEL8.
Figure 15:
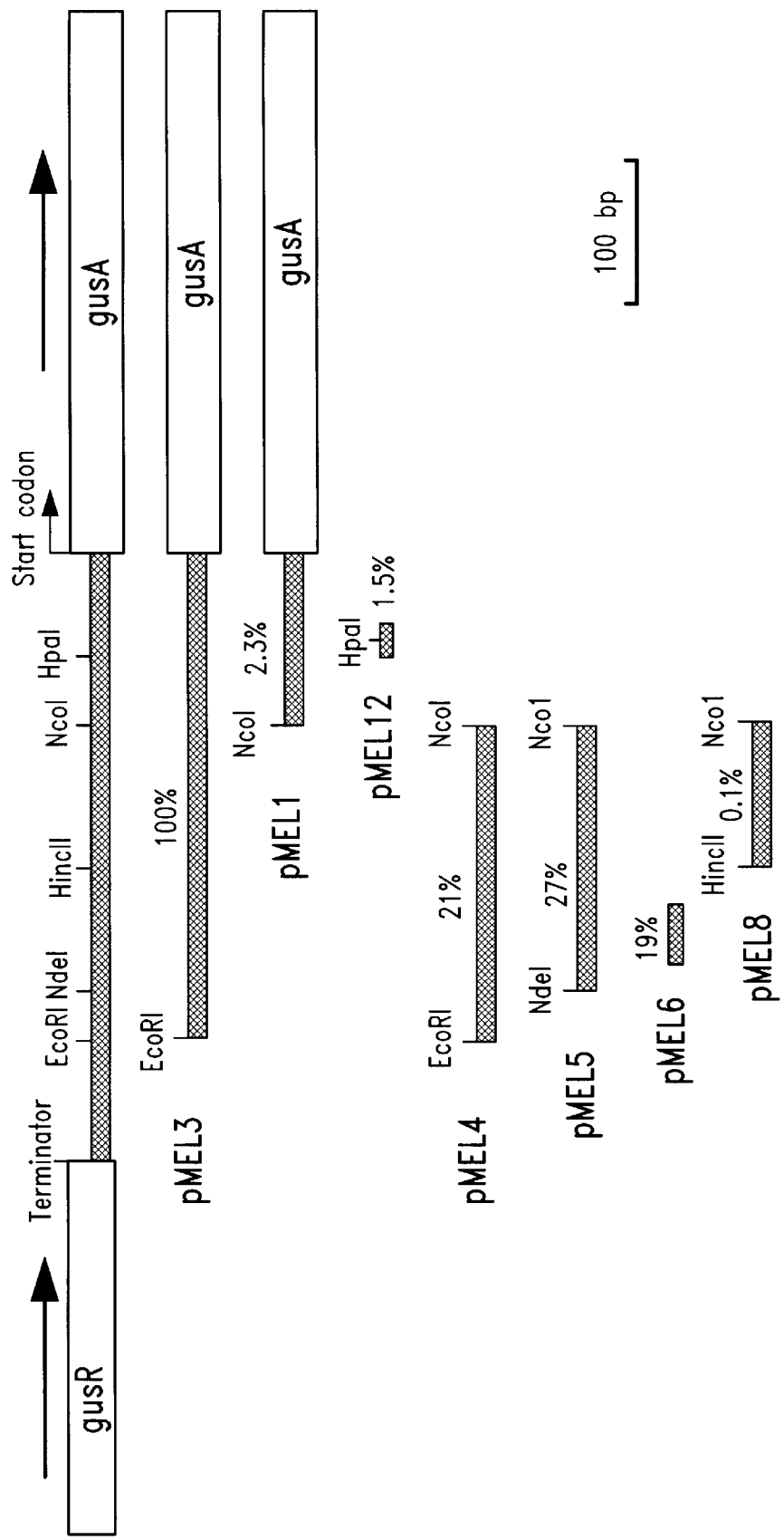
FIG. 15 diagrams subclones of the gus operon regulatory region and shows relative repressor titration of these subclones in DH5α expressed as a percentage of pKW244 titration.

A second approach that identifies operator sites of the gus operon is performed by synthesizing and cloning putative operator sequences directly into a pBSIISK+ vector and testing the clones for repressor binding by titration (FIG. 8 Three putative operator sequences, consisting of palindromic sequences, were identified from DNA sequence analysis.

One potential operator sequence is a 14 bp imperfect palindrome centered around an Hpa I site at +15 from the gus operon putative transcriptional start. A second, highly homologous (13 out of 14 base pairs) Hpa I palindrome is also present near the transcriptional start of the gusR gene. As the majority of repressors, including gusR are known to regulate themselves it was expected that a GusR operator site also exists.

Figure 16:
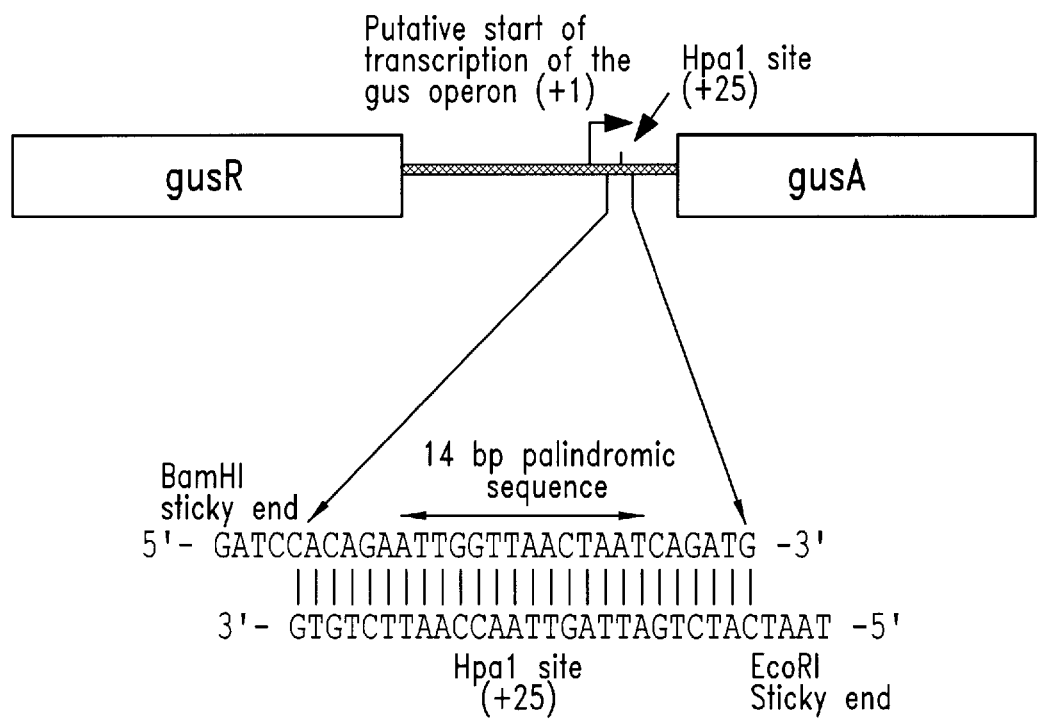
FIG. 16 depicts the location and sequence of the HpaI centered palindrome (SEQ ID NOS: 12 and 13) upstream of gusA.
Figure 17:
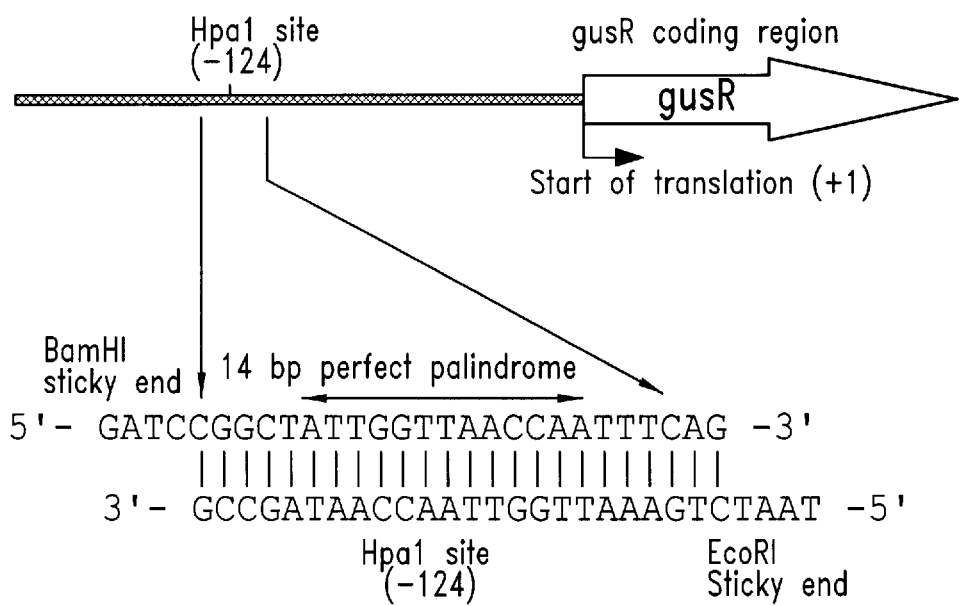
FIG. 17 depicts the location and sequence of the HpaI centered palindrome (SEQ ID NOS: 14 and 15) located upstream of gusR.

Both HpaI-centered sequences were cloned into pBSIISK+ (FIGS. 16 and 17). Two complementary oligonucleotides were synthesized and annealed. The double-stranded oligonucleotides had EcoRI and BamHI sticky ends, which were cloned into pBSIISK+ vector which had been prepared by digestion with EcoRI and BamHI. Clones containing these inserts were identified by titration of GUS activity in DH5α transformants plated on X-gluc plates and by the incorporation of the HpaI site in the resulting plasmid.

Figure 18:
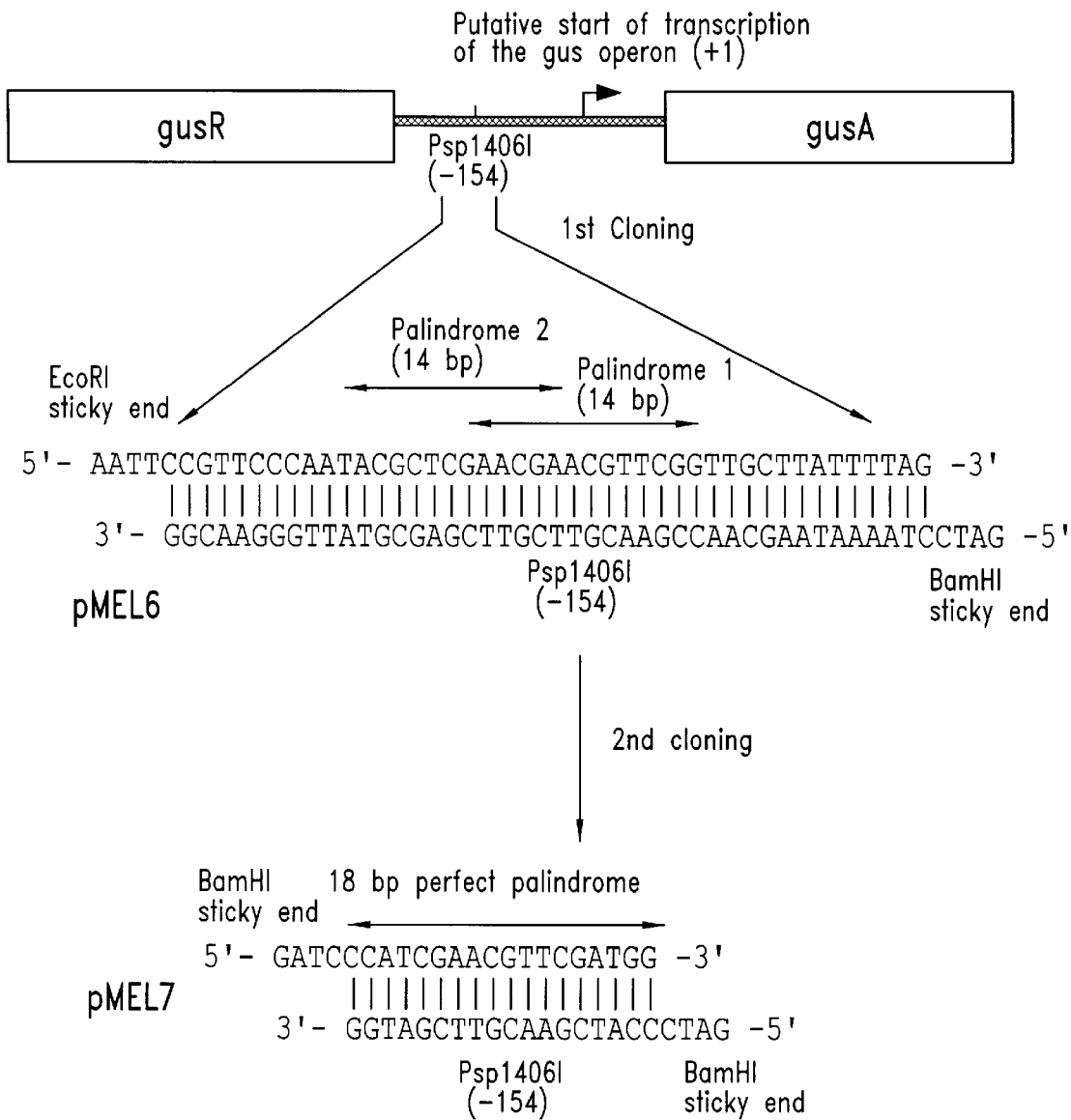
FIG. 18 depicts the location and sequence of the Psp1406I palindromes (SEQ ID NOS: 16–19) upstream of gusA.

Operator/repressor titration experiments performed on the various gus operon subclones discussed above suggested that a second region of DNA, separate from the HpaI palindrome discussed above, binds repressor molecules. This 75 bp region contains a 40 bp sequence containing two overlapping palindromes. (FIG. 18). A clone containing this region resulted in approximately 20% induction of the gus operon, indicating that it was sufficient to account for all repressor binding observed with pMEL4 and pMEL5 transformed DH5α. This further narrows down the positioning of a repressor binding sequence upstream of the transcriptional start to this particular fragment of DNA. Further analysis using a strain deleted for the uxu operon (ER1648; New England Biolabs, Beverly, Mass.) demonstrated that the uxu repressor accounts for less than 5% of gus operon repression.

This palindromic region was cloned into pBSIISK+ vector by complementary oligonucleotides which when annealed create EcoR I and BamH I sticky ends. Clones (pMEL6) were screened for by the titration of GUS activity in DH5α transformants plated on X-gluc plates. Candidate clones were verified by restriction digestion with Psp1406I. In addition, a perfect palindrome centered around the Psp1406I site was cloned into pBSIISK+ (pMEL7) to test for stronger repressor binding. Due to the nature of a perfect palindrome, only one oligonucleotide was synthesized, which created BamHI overhangs (see FIG. 18). Resultant clones were selected for by the loss of the α-complementation phenotype of the pBSIISK+ vector in DH5α transformants plated on Magenta-Gal (100 μg/ml) and verified by digestion with Psp1406I. This clone, pMEL7, resulted in very little titration when transformed into DH5α. The loss of repressor binding ability would seem to indicate that the true operator site within this region is the second palindrome, centered at −164 from the gus operon transcriptional start. However, in creating this 18 bp perfect palindrome, it is possible that nucleotides important to repressor binding to this region may have been replaced, thereby reducing the overall affinity of this site for a repressor molecule.

Figure 19:
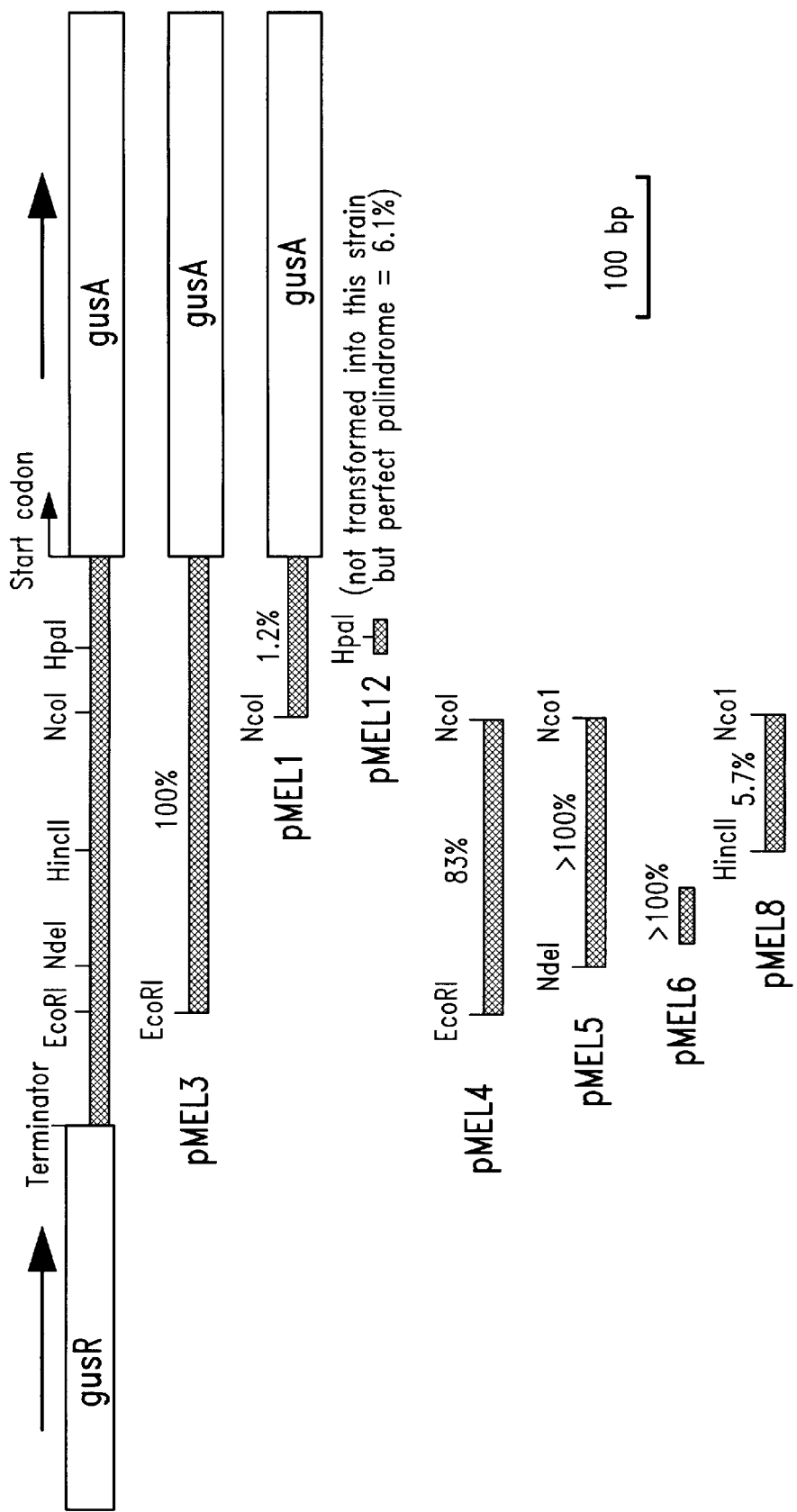
FIG. 19 diagrams subclones of the gus operon regulatory region and shows relative repressor titration of these subclones in ER1648, expressed as a percentage of pKW244 titration.

Identification of ERI 648 as an uxuR deletion strain allowed operator/repressor titration experiments performed with the gus operon regulatory sub-regions to be performed in a strain lacking the UxuR repressor. Any significant differences observed between these two systems could then be attributed to the absence of an UxuR titration effect. A number of the various gus operon regulatory region sub-clones were transformed into this strain. β-glucuronidase production was measured by the spectrophotometric GUS assay. Results of these titration experiments are recorded in the Table below and shown schematically in FIG. 19.

| Plasmid | Average amount of β-glucuronidase production (nmol pNP/min/mg protein) | 95% confidence limit | % of pKW244 β-glucuronidase production |
| --- | --- | --- | --- |
| pKW244 | 709 | 145 | 100 |
| pBSIISK+ | 35.2 | 5.2 | 5.0 |
| pMEL1 | 9.7 | 3.5 | 1.4 |
| pMEL3 | 583 | 131 | 82.2 |
| pMEL4 | 719 | 561 | >100% |
| pMEL5 | 753 | 219 | >100% |
| pMEL6 | 819 | 123 | >100% |
| pMEL34 | 43.3 | 16.3 | 6.1 |

When pMEL1 and pMEL34 were transformed into ER1648, no significant increase from the background beta-glucuronidase activity was detectable, suggesting that these plasmids were not titrating repressor away from the gus operon in this strain. As these plasmids contain the HpaI palindromic sequence shown to titrate repressor when transformed into DH5α, this indicates that the HpaI palindrome is an UxuR binding site.

In contrast, pMEL4, pMEL5 and pMEL6, all containing the major region of repressor binding regulating the gus operon showed a 5-fold increase in titration effect when transformed into this uxuR deletion strain, equaling that produced by pKW244 transformants.

Therefore, repressor/operator titration experiments performed with various sub-clones of the gus operon regulatory region have resulted in the identification of two repressor binding regions regulating the gus operon. A major binding region is located on a 44 bp fragment situated between −136 and −180 bp upstream of the gusA transcriptional start site, while a second, minor binding site is found in the HpaI centered imperfect palindrome located at +25 from this same start of transcription. This second binding site is an UxuR operator site.

Example 3

Expression of Gus Repressor Protein

Overexpression of gusR gene product is achieved by cloning the coding region in an expression vector. gusR gene is cloned into a variety of expression vectors by subcloning the gene from pKW223 and by amplification.

A. Expression of gusR as a lacZ fusion protein

Figure 20:
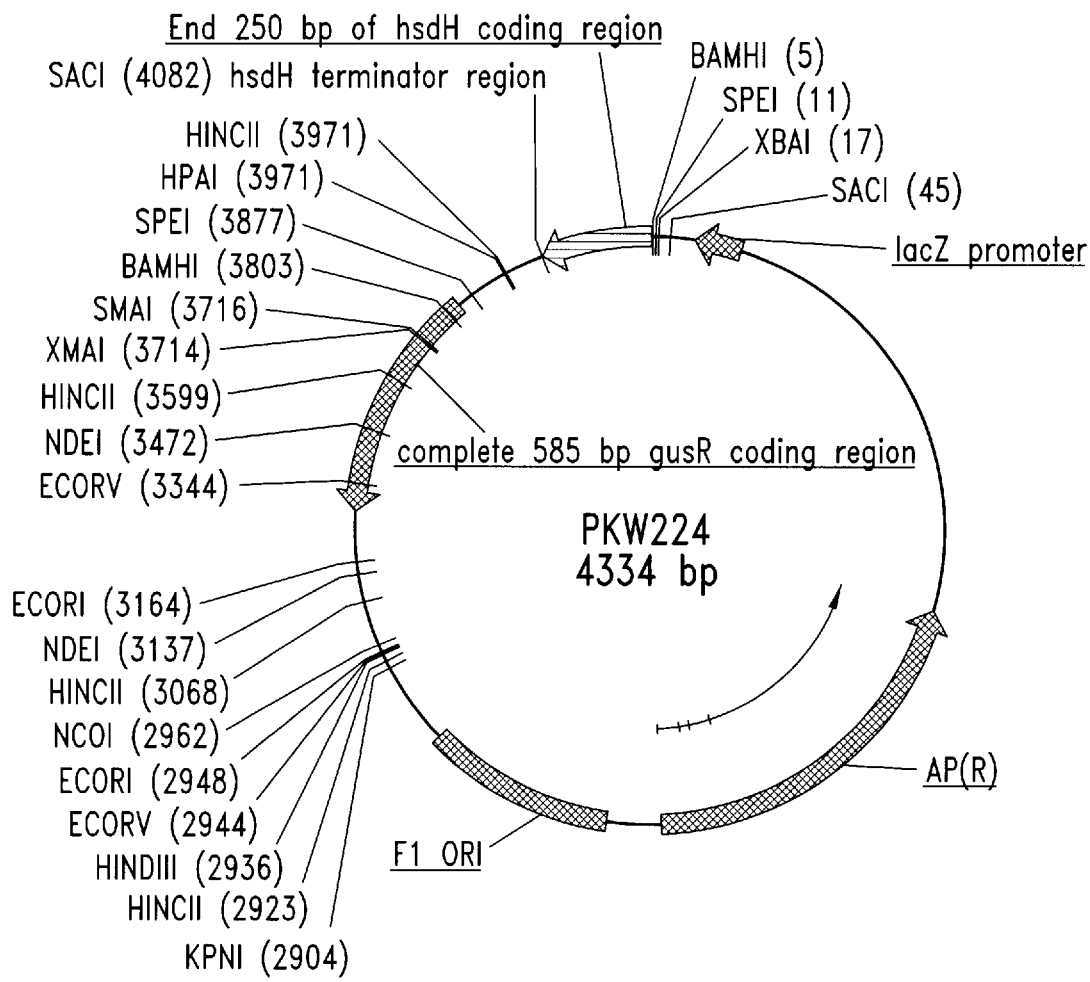
FIG. 20 shows a restriction map of pKW224.

The gusR gene was initially cloned in a 5'-3' transcriptional orientation downstream of the lac promoter in pBSIISK+ (pKW224) (FIG. 20). The fragment containing gusR had an additional 490 bp of upstream and 305 bp of downstream sequence. However, no GusR protein was detected when this plasmid was introduced into E. coli, suggesting that a sequence was hampering the expression of the gusR gene from the lacZ promoter. An inspection of the upstream sequence revealed an open reading frame found to contain the C-terminal coding region and the transcriptional terminator of the hsdH gene, involved in E. coli steroid metabolism (Yoshimoto et al, 1991). These sequences likely halted mRNA elongation and translation from the lacZ promoter prior to the gusR gene, located further downstream.

Figure 21:
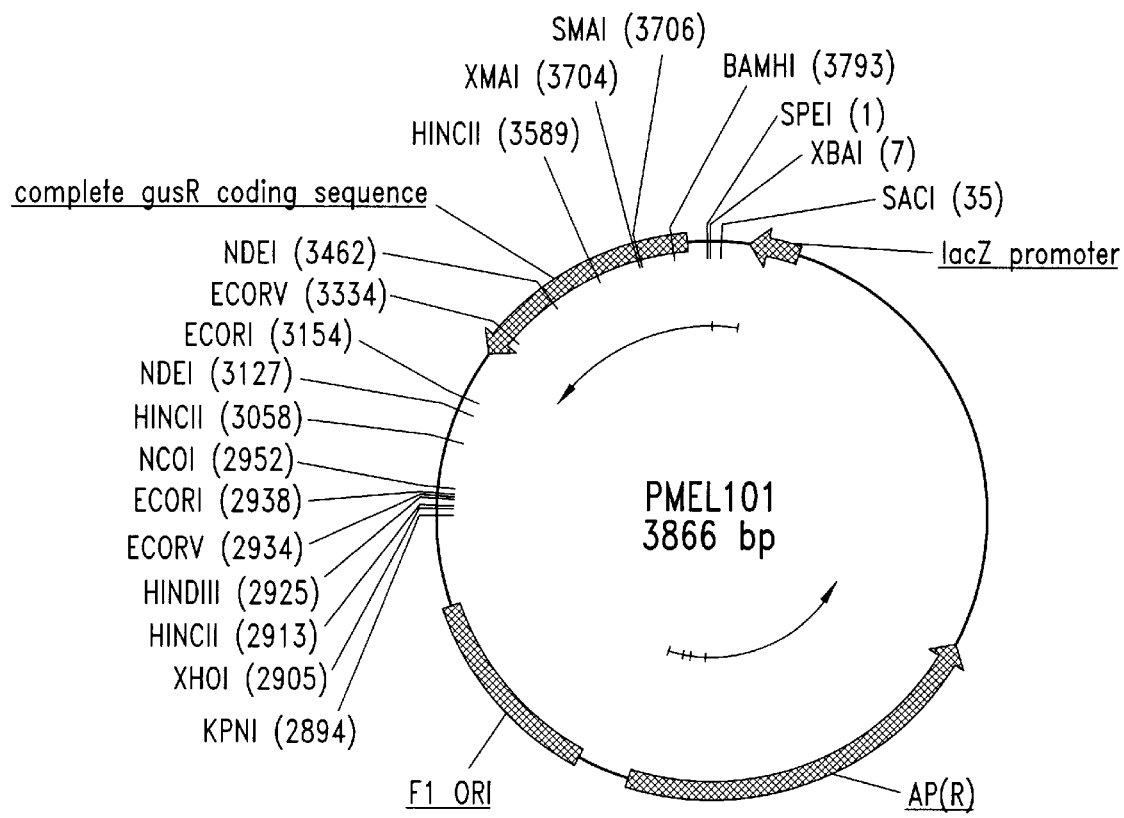
FIG. 21 shows a restriction map of pMEL101.
Figure 22:
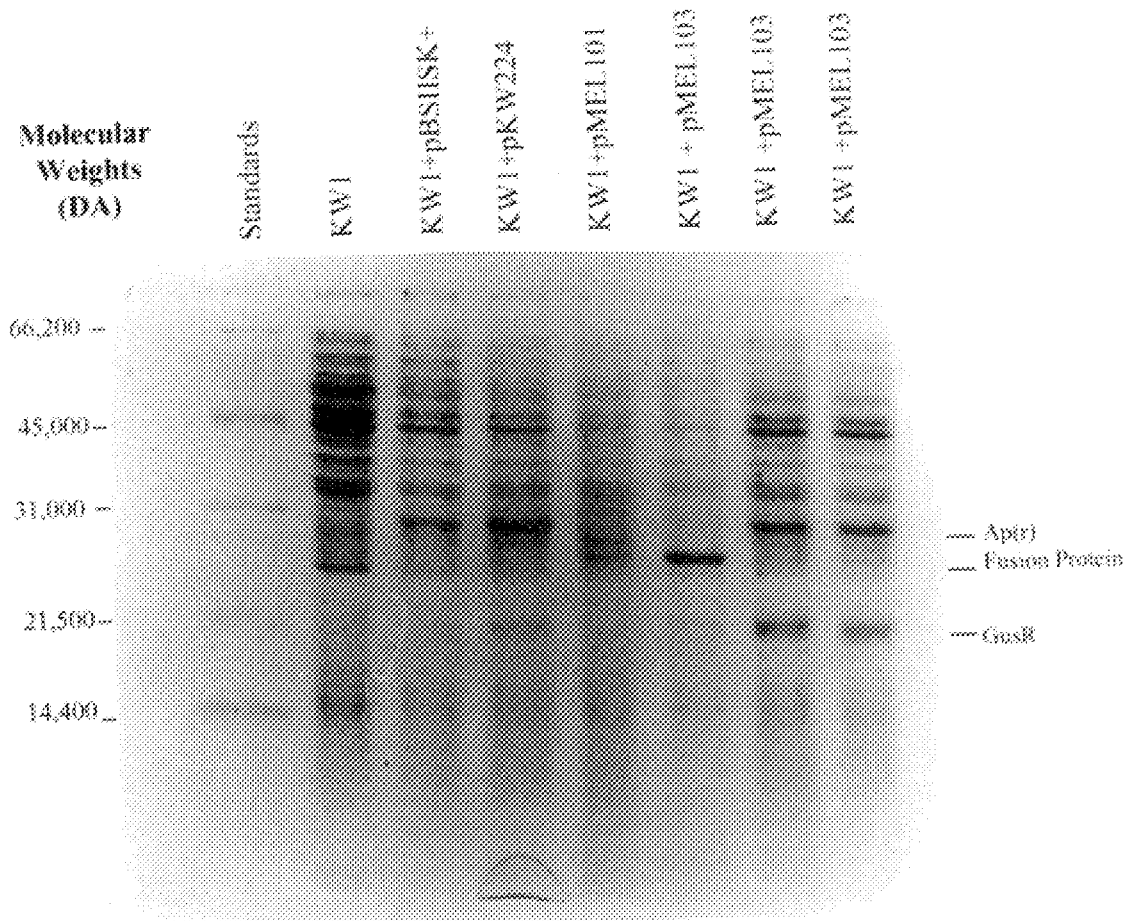
FIG. 22 is a photograph of a protein gel showing overexpression of a 26 kDa gusR/lacZ fusion protein from pMEL 101 and a 22 kDa gusR protein from pMEL103.

The hsd terminator was subsequently removed in the following manner. pKW224 was digested with Spe I, which cuts in the polylinker and 40 bp upstream of the putative translational start of gusR, releasing a 468 bp fragment containing the hsd terminator, leaving a 3866 bp fragment containing vector sequences and the gusR gene sequence in the same orientation as the lac promoter. Following ligation, clones lacking the 468 bp fragment were identified by amplification of a 1500 bp product using the T7 and reverse sequencing primers. Candidate clones were verified as lacking the Spe I site. One isolate was named pMEL101 (FIG. 21).

pMEL101 was transformed into *E. coli* strain KW1 (deleted for the gus operon) and induced for expression by 0.5 mM IPTG. A protein of about 26 kDa was clearly detected in pMEL101 transformed KW1, but was not detected in protein extracts from wild-type KW1, pBSIISK+ -transformed KW1, or pKW224-transformed KW1 (FIG. 22). A 26 kDa protein is the predicted mass of a fusion protein formed between the 22 kDa GusR protein and the lacZ coding sequence upstream of this gene in pMEL101.

GusR was also amplified with the primer pair (SEQ ID NOS: 8 and 9):

5'-CGAGAATTCGAGGAGTCCATCATGATG-GATAACATGCAGACTGAAG-3'

5'-GCTGAATTCAAGCTTCAGGATGCGGT-TAAGATACCGCC-3'

Figure 24:
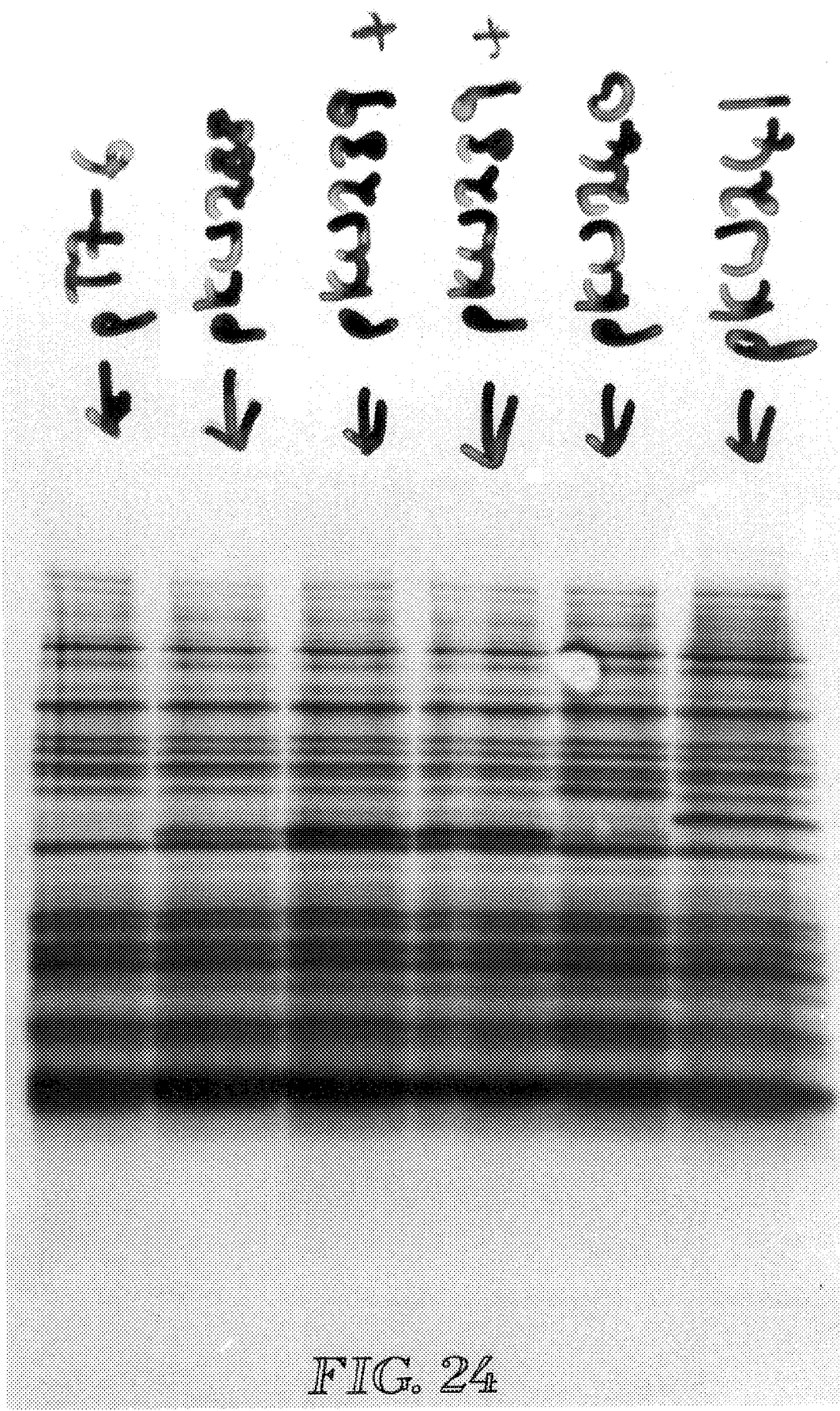
FIG. 24 is a photograph of protein gel showing overexpression of a 26 kDa gusR/lacZ fusion protein (indicated with arrow on right side) from pKW241 and a 22 kDa gusR protein (indicated with arrow on left side) from pKW288 and pKW289.

The 5' primer (upper primer; SEQ ID NO: 8) contains an EcoRI site and a strong Shine-Dalgarno sequence. The 3' primer (lower primer; SEQ ID NO: 9) contains an EcoRI site. The amplified product was digested with EcoRI and inserted into a vector either to give as a lacZ fusion or a non-fusion protein. FIG. 24 shows that the predicted 22 kDa (non-fusion) and 26 kDa (fusion) proteins were produced.

Figure 23:
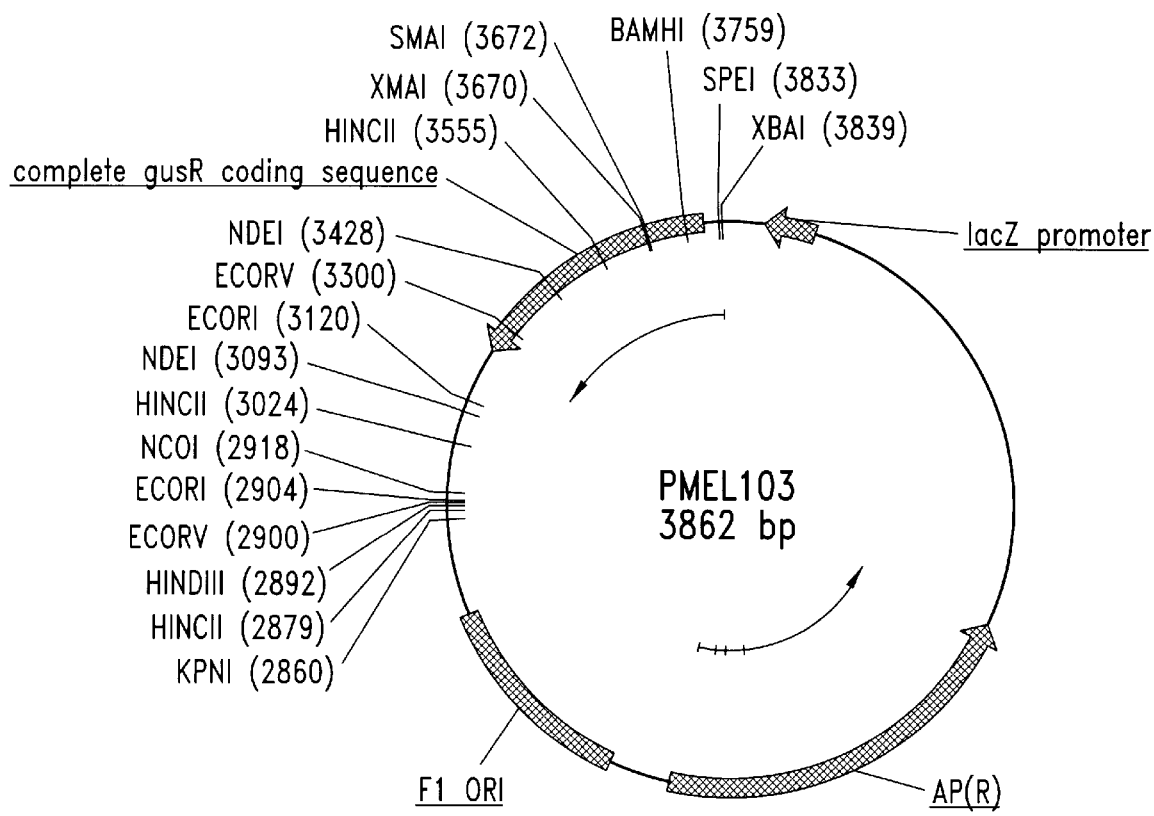
FIG. 23 shows a restriction map of pMEL103.

B. Expression of gusR as a non-fusion protein in pMEL101 derivative pMEL101 was engineered to create a frameshift in the fusion protein leading to the creation of two stop codons in frame with lacZ and just upstream of the gusR gene. The translational stop codons would force the detachment of ribosomes from the mRNA transcript at this site and their reattachment at the nearby gusR start of translation. As such, the expression of wild-type GusR protein would ensue. pMEL103 was constructed by digestion of pMEL101 with Sac I, a site located in the polylinker, removal of the sticky ends by digestion with T4 DNA polymerase. The treated plasmid was religated, transformed into KW1, and a clone with the desired configuration was isolated (pMEL103) (FIG. 23). SDS-PAGE analysis of protein extracts of pMEL 103-transformed KW1 showed the overexpression of a 22 kDa GusR protein. However, genetic tests showed that despite the expression of GusR, no large decrease was seen in GUS activity, which was expected after induction with IPTG. An examination of the DNA sequence downstream of the frameshift identified a second *E. coli* start codon (GTG) 12 codons upstream of the gusR translational start. Ribosomal reattachment may therefore be occurring preferentially at this site, rather than at the gusR start of translation, to produce an inactive fusion protein. This is likely considering the lack of a strong Shine-Dalgarno sequence regulating the gusR gene.

C. Expression of gusR as a hexa-His fusion protein

The coding region of gusR is amplified and inserted into an expression vector. The vector is a derivative of pTTQ18 (Stark, *Gene* 51: 255, 1987) in which an NcoI site was engineered downstream of a strong Shine-Dalgarno sequence, and an NheI site adjacent to six His codons was also engineered. The primers used in the amplification reaction are as follows:

gusR-0528T (SEQ ID NO: 10) 5'-GACCAGGTTACCATGGATM-CATGCAGACTGMGCAC-3' gusR-0528B (SEQ ID NO: 11) 5'-GACGTGATGGTGGCTAGCG-GATGCGGTTMGATACCGCCMATC-3'

The resulting amplified product (and the native product) uses the second methionine as a translational start and contains an Nco I site (underlined in 0528T) at the 5' end to facilitate cloning, as well as an NheI site at the 3' end (underlined in 0528B) such that the product is inserted in-frame with vector sequence encoding 6 His residues at the C-terminal end. The nucleotides identical or complementary to gusR are in bold. gusR is amplified from pMEL101, and inserted into a vector. Protein is produced and isolated by nickel-chromatography.

D. Purification of glucuronidase repressor protein

Suitable bacterial hosts (e.g., *E. coli* JM105; XL-1 Blue) are transformed with a vector construct that is capable of expressing a glucuronidase repressor. Preferred vectors allow induction of expression upon addition of ITPG. Some suitable vectors are described above, others are well known and readily available. Following induction and a suitable growth period, the cells are harvested and lysed by agitation with glass beads. The lysate is clarified by centrifugation and batch absorbed on a glucuronide-chromatography matrix, phenylthio-β-D-glucuronide (PTG)-Sepharose CL6B or saccharolactone-agarose for gusR, or Ni-IDA-Sepharose for His$_6$-gusR fusion. The columns are either procured commercially or synthesized by linkage using carbodiimide chemistry. The matrix is poured into a column and washed with buffer, typically either 50 mM Tris pH 7.6, 1 mM DTT; 50 mM MES pH 7.0, or IMAC buffer (for hexa-his fusions). The repressor bound to the matrix is eluted in NaCl containing buffer.

Figure 25:
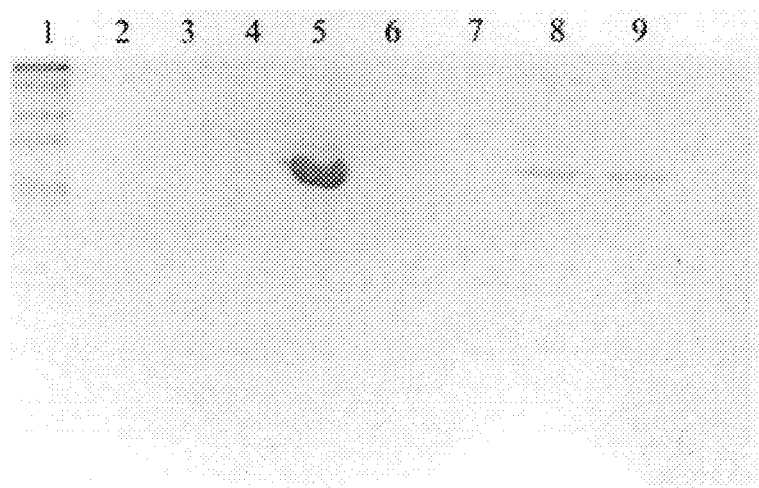
FIG. 25 is a computer image of a protein gel showing purification of gusR on a Sepharose CL6B column coupled with phenylthio-β-D-glucuronide. Lane 1, protein size markers; lane 2, sample flow-through; lane 3, fraction collected from first buffer wash; lane 4, fraction collected from second buffer wash; lane 5, gusR standard; lane 6, first fraction collected from elution with 0.1M NaCl; lane 7, second fraction collected from elution with 0.1M NaCl; lane 8, first fraction collected from elution with 0.3M NaCl; lane 9, second fraction collected from elution with 0.3M NaCl.
Figure 26:
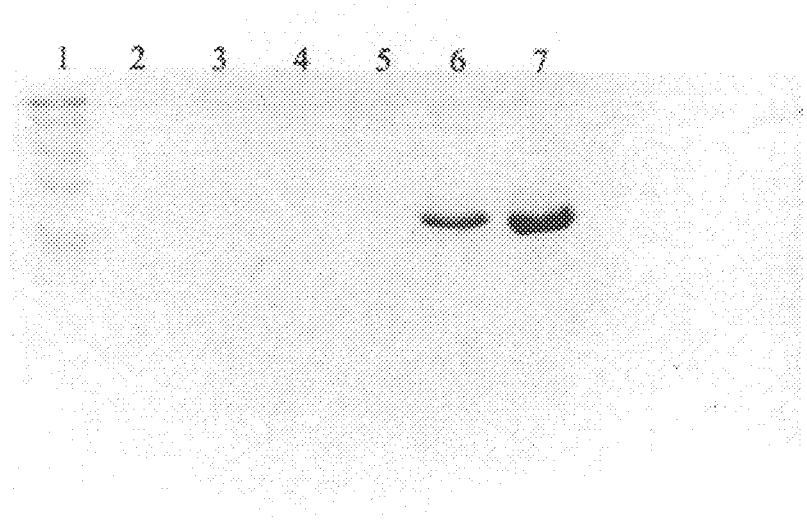
FIG. 26 is a computer image of a protein gel showing purification of gusR on an agarose column coupled with saccharolactone. Lane 1, protein size markers; lane 2, sample flow-through; lane 3, fraction collected from first buffer wash; lane 4, fraction collected from second buffer wash; lane 5, fraction collected from elution with 0.1M NaCl; lane 6, second fraction collected from elution with 0.5M NaCl; lane 7, gusR standard.
Figure 27:
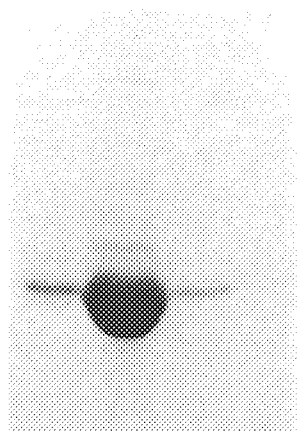
FIG. 27 is a computer image of a protein gel showing purification of hexahistidine-modified gusR from an induced culture on a SEPHAROSE column coupled with nickel. Lane 1, first elution using 10 mM EDTA in IMAC buffer; lane 2, second elution using 10 mM EDTA in IMAC buffer; lane 3, third elution using 10 mM EDTA in IMAC buffer.

As shown in FIGS. 25, 26, and 27, purified repressor protein is readily obtainable by these methods. gusR is substantially eluted from saccharolactone-agarose in 0.1M NaCl and also in 0.5M NaCl (FIG. 26) and is substantially eluted from PTG-Sepharose at 0.3M NaCl (FIG. 25). Hexa-HisgusR is eluted from Ni-IDA-Sepharose in 10 mM EDTA (FIG. 27).

Example 4

Induction of Gus by β-Glucuronides in Wild-Type *E. coli*

Various β-glucuronides are tested for their ability to induce GUS activity. These inducers include steroid glucuronides. Wild-type *E. coli* is isolated from feces and grown to mid-log phase. Inducer is added at 1 mM for 60 min. The cells are washed and GUS activity determined. The following table indicates that natural β-glucuronides found in vertebrates induce the gus operon. Moreover, there is no correlation between the molecular weight of the inducer and its inducing ability.

| INDUCER | Mol. Wt. | INDUCTION (%) |
| --- | --- | --- |
| None | — | <0.5 |
| phenyl glucuronide | 270 | 100 |
| o-aminophenyl glucuronide | 285 | 95 |
| p-nitrophenyl glucuronide | 315 | 68 |
| 4-methylumbelliferyl glucuronide | 352 | 89 |
| 3-cyanoumbelliferyl glucuronide | 338 | 84 |
| tryptophyl glucuronide | 380 | 85 |
| 5-bromo-4-chloro-3-indolyl glucuronide | 521 | 99 |
| hydroxyquinoline glucuronide | 321 | 21 |

| INDUCER | Mol. Wt. | INDUCTION (%) |
|---|---|---|
| naphthol ASBI glucuronide | 548 | 12 |
| phenolphthalein glucuronide | 493 | 13 |
| estriol-3-glucuronide | 464 | 13 |
| estriol-17-glucuronide | 464 | 11 |
| estrone-17-glucuronide | 464 | 13 |
| testosterone-glucuronide | 464 | 12 |
| pregnanediol-glucuronide | 497 | 11 |

A biological indicator for detecting the presence and concentration of glucuronides in a sample, such as urine, blood, bile, cell extracts, and the like, can be constructed. Briefly, the gusA gene in any of the vector constructs expressing gusA under control of the glucuronidase promoter/operator region is replaced with the coding region of another reporter gene. Suitable reporter genes are well known, their sequences available or clones containing the genes available. These reporter genes include, β-gal, luciferase, green fluorescent protein and the like. The engineered construct, which has a synthetic operon, is introduced into a host cell, such as bacteria, plant cell, animal cell, fungal cell, or any cell line. Preferably, the host cell lacks endogenous GUS activity and expresses a glucuronide transport molecule or is able to transport the glucuronide across a cell membrane. The synthetic operon is thus induced by a glucuronide but the induced gene does not cleave a glucuronide.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

BRIEF DESCRIPTION OF THE SEQUENCE LISTING

SEQ ID No. 1 is a nucleotide sequence which encodes a glucuronide repressor.

SEQ ID No. 2 is a predicted amino acid sequence of *E. coli* gusR.

SEQ ID No. 3 is a nucleotide sequence of the intergenic region between gusR and gusA that contains promoter/operator sequence.

SEQ ID No. 4 is a nucleotide sequence of the gus operon.

SEQ ID No. 5 is the predicted amino acid sequence of *E. coli* gusA.

SEQ ID No. 6 is a predicted amino acid sequence of *E. coli* gusB.

SEQ ID No. 7 is a predicted amino acid sequence of *E. coli* gusC.

---

We claim:

1. An isolated nucleic acid molecule consisting of the sequence presented in SEQ ID NO: 1.

2. A high copy number vector, comprising a nucleic acid molecule encoding a glucuronide repressor according to any one of claim 1.

3. An isolated nucleic acid molecule encoding a polypeptide consisting of a domain of a glucuronide repressor that binds a glucuronidase operator.

4. The nucleic acid molecule of claim 3 wherein the nucleic acid molecule consists of the sequence of nucleotides 1 to 192 of SEQ ID No: 1.

5. The nucleic acid molecule of claim 3 wherein the nucleic acid molecule encodes a polypeptide consisting of amino acids 1–63 of SEQ ID No: 2.

6. An isolated nucleic acid molecule encoding polypeptide consisting of a domain of a glucuronide repressor that binds a glucuronide.

7. The nucleic acid molecule of claim 6 wherein the nucleic acid molecule consists of the sequence of nucleotides 192 to 462 of SEQ ID NO: 1 or nucleotides 195 to 585 of SEQ ID NO: 1.

8. The nucleic acid molecule of claim 6 wherein the nucleic acid molecule encodes a polypeptide consisting of amino acids 64 to 154 of SEQ ID NO: 2 or amino acids 64 to 195 of SEQ ID NO:2.

9. A vector, comprising a nucleic acid molecule encoding a glucuronide binding domain from a glucuronide repressor according to claim 6.

10. A vector, comprising a nucleic acid molecule encoding a fusion protein comprising a glucuronide binding domain from a glucuronide repressor and a DNA-binding domain that binds to a selected nucleotide sequence.

11. A vector according to a any one of claims 2–10 wherein the vector further comprises a heterologous promoter and is an expression vector.

12. The vector of claim 11 wherein the vector is a binary *Agrobacterium tumefaciens* plasmid vector.

13. A host cell containing a vector according to claims 2–10.

14. The host cell of claim 13, wherein the cell is a plant cell.

15. The host cell of claim 13, wherein the cell is an animal cell.

16. The host cell of claim 13, wherein the cell is a fungal cell.

17. The host cell of claim 13, wherein the cell is a bacterial cell.

18. A method for isolating a glucuronide transport protein, comprising:

(a) transfecting or transforming a cell that does not transport a glucuronide with a nucleic acid molecule encoding a glucuronide repressor and a reporter gene linked to a glucuronide operator;

(b) further transfecting or transforming the cell in step (a) with an expression library constructed from vertebrate nucleic acid;

(c) treating the cell in step (b) with a glucuronide; and (d) detecting expression of the reporter gene, thereby identifying a cell expressing a transport protein.

19. An expression vector, comprising a nucleic acid sequence encoding a glucuronide repressor under the control of a heterologous promoter.

20. The expression vector of claim 19 wherein the nucleic acid sequence of the glucuronide repressor comprises the sequence presented in SEQ ID NO:1 or variant thereof and which encodes a functional glucuronide repressor.

21. The expression vector of claim 19 wherein the nucleic acid sequence of the glucuronide repressor encodes SEQ ID NO:2 or variant thereof and which encodes a functional glucuronide repressor.

22. An expression vector, comprising a nucleic acid sequence encoding a domain of a glucuronide repressor that binds a glucuronidase operator under the control of a heterologous promoter.

23. The expression vector of claim 22 wherein the nucleic acid sequence comprises the sequence of nucleotides 1 to 192 of SEQ ID NO:1 or a variant thereof, and which encodes a domain that binds a glucuronidase operator.

24. The nucleic acid sequence of claim 22 wherein the nucleic acid sequence encodes a polypeptide consisting of amino acids 1 to 63 of SEQ ID NO:2 or a variant thereof, and which encodes a domain that binds a glucuronidase operator.

25. An expression vector, comprising a nucleic acid sequence encoding a domain of a glucuronide repressor that binds a glucuronide under the control of a heterologous promoter.

26. The nucleic acid sequence of claim 25 wherein the nucleic acid sequence comprises the sequence of nucleotides 192 to 462 of SEQ ID NO:1 or a variant thereof, or nucleotides 195 to 585 of SEQ ID NO:1 or a variant thereof and which encodes a domain that binds a glucuronide.

27. The nucleic acid sequence of claim 25 wherein the nucleic acid sequence encodes a polypeptide consisting of amino acids 64 to 154 of SEQ ID NO:2 or a variant thereof, or amino acids 64 to 195 of SEQ ID NO:2 or a variant thereof and which encodes a domain that binds a glucuronide.

28. The expression vector of any one of claims 19–27, wherein the vector is a binary *Agrobacterium tumefaciens* plasmid vector.

29. The expression vector of any one of claims 19–27, wherein the vector is a bacterial vector.

30. The expression vector of any one of claims 19–27, wherein the heterlogous promoter is functional in a plant cell.

31. The expression vector of any one of claims 19–27, wherein the heterologous promoter is functional in a bacterium.

32. The expression vector of any one of claims 19–27, wherein the heterologous promoter is functional in a fungal cell.

33. The expression vector of any one of claims 19–27, wherein the heterologous promoter is functional in an animal cell.

34. A host cell containing the expression vector according to any of claims 19–27.

35. The host cell of claim 34 wherein the cell is a plant cell.

36. The host cell of claim 34 wherein the cell is an animal cell.

37. The host cell of claim 34 wherein the cell is a fungal cell.

38. The host cell of claim 34 wherein the cell is a bacterial cell.

* * * * *

UNITED STATES PATENT AND TRADEMARK OFFICE
CERTIFICATE OF CORRECTION

PATENT NO. : 5,879,906

DATED : March 9, 1999

INVENTOR(S) : Richard A. Jefferson, et al.

It is certified that error appears in the above-identified patent and that said Letters Patent is hereby corrected as shown below:

On the title page, Item [75], remove "Michael Leader" as an inventor.

Signed and Sealed this

Twenty-sixth Day of October, 1999

*Attest:*

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.    : 5,879,906
DATED         : March 9, 1999
INVENTOR      : Richard A. Jefferson and Katherine J. Wilson It is certified that an error appears in the above identified patent and that said Letters Patent is hereby corrected as shown below:

In the Claims:

In column 50, line 31, claim 24, after the first word please delete "nucleic acid sequence of claim 22" and thereby insert -- expression vector of claim 22--.

In column 50, line 39, claim 26, after the first word please delete "nucleic acid sequence of claim 25" and thereby insert -- expression vector of claim 25--.

In column 50, line 44, claim 27, after the first word please delete "nucleic acid sequence of claim 25" and thereby insert -- expression vector of claim 25 -- .

Signed and Sealed this

Eighth Day of February, 2000

*Attest:*

Q. TODD DICKINSON

*Attesting Officer*      *Commissioner of Patents and Trademarks*